(12) United States Patent
Kataguchi

(10) Patent No.: US 8,684,932 B2
(45) Date of Patent: Apr. 1, 2014

(54) ULTRASONIC DIAGNOSTIC APPARATUS, ULTRASONIC DIAGNOSTIC METHOD, AND CONTROL PROCESSING PROGRAM FOR ULTRASONIC DIAGNOSTIC APPARATUS

(75) Inventor: Muneki Kataguchi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1658 days.

(21) Appl. No.: 11/754,053

(22) Filed: May 25, 2007

(65) Prior Publication Data

US 2008/0009727 A1 Jan. 10, 2008

(30) Foreign Application Priority Data

May 30, 2006 (JP) ................................. 2006-149621

(51) Int. Cl.
*A61B 8/00* (2006.01)
(52) U.S. Cl.
USPC .......................................................... 600/441
(58) Field of Classification Search
USPC .......................................................... 600/441
See application file for complete search history.

(56) References Cited

U.S. PATENT DOCUMENTS

| 5,029,082 | A  | * | 7/1991  | Shen et al. ..................... | 600/512 |
|-----------|----|---|---------|-----------------------------------|---------|
| 6,423,006 | B1 | * | 7/2002  | Banjanin ........................ | 600/453 |
| 6,673,020 | B2 | * | 1/2004  | Okada et al. .................... | 600/454 |
| 7,534,209 | B2 | * | 5/2009  | Abend et al. ................... | 600/454 |
| 2002/0058874 | A1 | * | 5/2002  | Ono et al. ..................... | 600/476 |
| 2003/0216645 | A1 | * | 11/2003 | Yao et al. ...................... | 600/437 |

FOREIGN PATENT DOCUMENTS

| JP | 6-217975 | | 8/1994 |
| JP | 06-217975 | * | 9/1994 |
| JP | 9-10211 | | 1/1997 |
| JP | 10-323349 | | 12/1998 |
| JP | 2000-166926 | | 6/2000 |
| JP | 2003-523250 | | 8/2003 |
| JP | 2005-87293 | | 4/2005 |
| WO | WO 01/62155 A1 | | 8/2001 |
| WO | WO 2005/041759 A2 | | 5/2005 |

OTHER PUBLICATIONS

Office Action issued Jul. 26, 2011 in Japan Application No. 2006-149621.

* cited by examiner

*Primary Examiner* — Tse Chen
*Assistant Examiner* — Hien Nguyen
(74) *Attorney, Agent, or Firm* — Oblon, Spivak, McClelland, Maier & Neustadt, L.L.P.

(57) ABSTRACT

An ultrasonic diagnostic apparatus including a multi-thresholding unit that performs multi-thresholding on the volume data of the blood flow speed on the basis of a reference value related to the blood flow speed. A surface extraction unit extracts a surface of the blood flow on the basis of the multi-threshold volume data. A weighting unit performs a weighting used for calculating the position of the center of gravity for the blood flow region formed by the blood flow surface. A center of gravity position calculation unit calculates a position of the center of gravity of the blood flow region. The Doppler sample marker position setting unit sets the position of the Doppler sample marker to the position of the center of gravity for the blood flow region. A Doppler sample marker movement control unit controls movement of the Doppler sample marker on the basis of the Doppler sample marker position setting data.

15 Claims, 16 Drawing Sheets

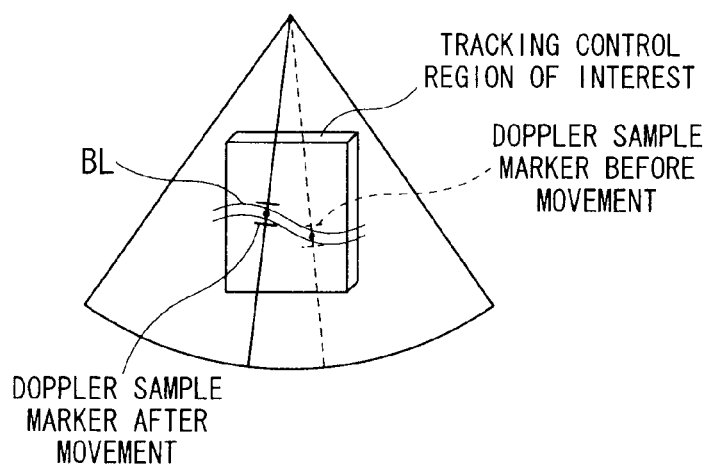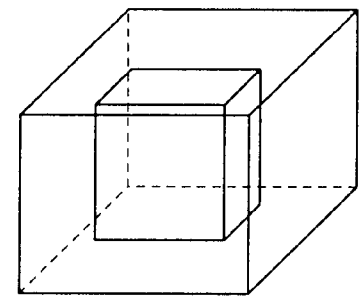
FIG. 13A    FIG. 13B
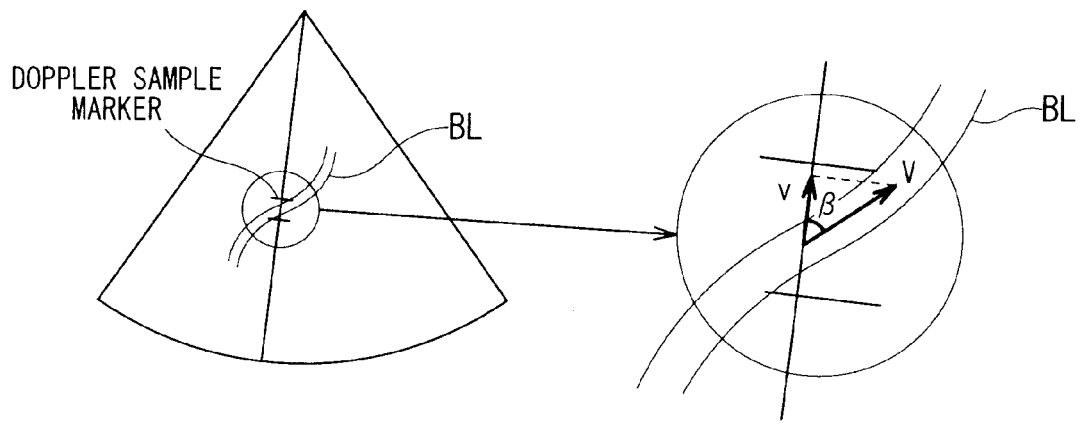
FIG. 14

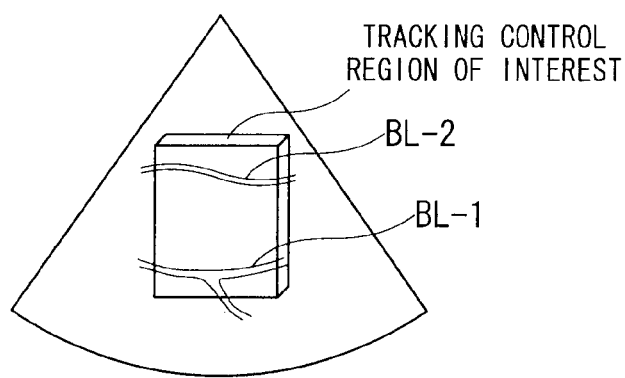 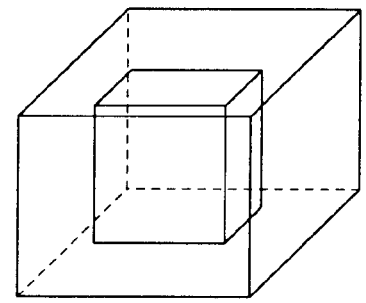
FIG. 15A          FIG. 15B
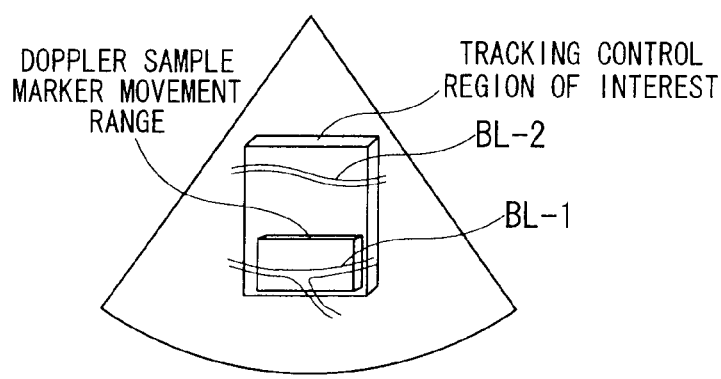 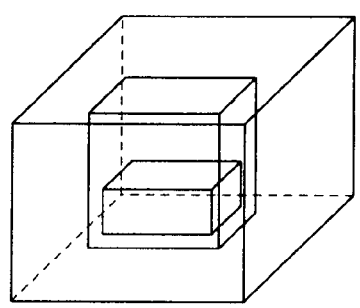
FIG. 16A          FIG. 16B

ULTRASONIC DIAGNOSTIC APPARATUS, ULTRASONIC DIAGNOSTIC METHOD, AND CONTROL PROCESSING PROGRAM FOR ULTRASONIC DIAGNOSTIC APPARATUS

BACKGROUND OF THE INVENTION

1. Field of the Invention

The present invention relates to an ultrasonic diagnostic apparatus, an ultrasonic diagnostic method, and a control processing program for the ultrasonic diagnostic apparatus, in particular, an ultrasonic diagnostic apparatus, an ultrasonic diagnostic method, and a control processing program for the ultrasonic diagnostic apparatus in which tracking of a sample marker of spectrum Doppler can be performed in accordance with movement of a blood vessel.

2. Description of the Related Art

In recent years, an ultrasonic diagnostic apparatus has been proposed which is capable of displaying a tomographic image (a B mode tomographic image) and blood flow information in real time by using an ultrasonic Doppler method, an ultrasonic pulse reflection method, and other methods in combination.

The ultrasonic Doppler method used in combination with the ultrasonic pulse reflection method can be roughly divided into two methods: a spectrum Doppler method of displaying a temporal change in a Doppler frequency corresponding to the speed of the blood current and a color Doppler method of color displaying information such as the blood current speed and variance.

When blood flow information inside the blood vessel or the like is observed by using the spectrum Doppler method, in order to observe blood flow information of a desired blood vessel, a sample marker for detecting the blood flow information of the desired position needs to perform a tracking in accordance with a movement of the desired blood vessel. For that reason, up to now, as a method of tracking the sample marker, a doctor or a technician (hereinafter referred to as "operator") manually performs an adjustment of the position of the sample marker so that the position of the sample marker is matched to the moved position of the blood vessel desired to be observed.

However, in a case where, for example, a coronary artery (blood vessel) present in the vicinity of the heart is observed with use of the manual tracking method by the operator, as the coronary artery relatively largely moves along with a beat of the heart, it is difficult for the operator to adjust the position of the sample marker in accordance with the movement of the coronary artery (blood vessel) for allowing the sample marker to track the coronary artery (blood vessel).

Also, the position of the blood vessel is moved due to a breathing, a motion, or the like of a patient (hereinafter referred to as "subject body"). Therefore, the operator needs to frequently perform an adjustment of the position of the sample marker and there is a problem of the troublesome adjustment operation.

In view of the above, an ultrasonic diagnostic apparatus has been proposed in which the automatic tracking of the sample marker can be performed in accordance with the observation position, operational burdens on the operation can be alleviated, and it is possible to shorten the diagnosis time.

According to an ultrasonic diagnostic apparatus proposed in Japanese Unexamined Patent Application Publication No. 6-217975, the automatic tracking of the sample marker is performed with use of blood flow information of a color Doppler in a two dimensional fault, and even when the blood vessel is moved, blood flow information of the blood vessel desired to be observed can be obtained.

Also, such an ultrasonic diagnostic apparatus has been proposed that a blood flow direction is automatically detected in addition to the automatic tracking of the sample marker and a Doppler angle is calculated on the basis of the detected blood flow direction to suppress an error to minimum due to mismatching between a direction of an ultrasonic wave beam and the blood flow direction.

According to an ultrasonic diagnostic apparatus proposed in PCT Japanese Translation Patent Publication No. 2003-523250, a measurement accuracy for a blood flow speed can be increased.

However, in the ultrasonic diagnostic apparatuses proposed in Japanese Unexamined Patent Application Publication No. 6-217975 and PCT Japanese Translation Patent Publication No. 2003-523250, the automatic tracking in the two dimensional fault is performed while using a plurality of ultrasonic wave transducer elements arranged in an array in a one dimensional manner. Thus, the tracking is possible with respect to the blood vessel movement in the two dimensional cross-section. However, the blood vessel inside the subject body moves in a three dimensional manner including a depth direction with respect to the cross-section. When the blood vessel desired to be observed moves in the depth direction with respect to the cross-section, it is difficult to perform the tracking of the sample marker in accordance with the movement of the blood vessel.

In particular, when a diagnosis is performed after administration of a medicine to the subject body, the blood vessel inside the subject body largely moves in a three dimensional manner including the depth direction with respect to the fault plane as compared with a normal condition, and it is more difficult to perform the tracking of the sample marker in accordance with the movement of the blood vessel desired to be observed.

SUMMARY OF THE INVENTION

Accordingly, the present invention has been made in view of the circumstances encouraged in the prior art mentioned above, and it is an object of the present invention to provide an ultrasonic diagnostic apparatus, an ultrasonic diagnostic method, and a control processing program for the ultrasonic diagnostic apparatus in which tracking of a sample marker of a spectrum Doppler can be easily and accurately performed in accordance with a three dimensional movement of a blood vessel desired to be observed.

In order to solve the above-mentioned problems, an ultrasonic diagnostic apparatus according to an aspect of the present invention includes a volume data generation unit configured to oscillate oscillating a plurality of ultrasonic wave transducer elements to transmit ultrasonic waves and to receive reflection waves which are reflected from a subject body and generate volume data related to a fluid inside the subject body on the basis of reception signals obtained by converting the reflection waves by the ultrasonic wave transducer elements; a fluid region calculation unit configured to calculated fluid region where the volume data satisfies a predetermined condition among the fluid in the subject body; a position calculation unit configured to calculate a predetermined position in the fluid region; a sample marker position setting unit configured to set a position of a sample marker to the predetermined position calculated by the position calculation unit; a sample marker movement control unit configured to control a movement of the position of the sample marker on the basis of sample marker position setting data set by the sample marker position setting unit; and a transmission and reception control unit configured to perform a control such that ultrasonic waves are transmitted and received at the position of the sample marker whose movement is controlled by the sample marker movement control unit.

In order to solve the above-mentioned problems, an ultrasonic diagnostic method according to an aspect of the present invention includes a volume data generation step of oscillating a plurality of ultrasonic wave transducer elements to transmit ultrasonic waves and to receive reflection waves which are reflected from a subject body and generating volume data related to a fluid inside the subject body on the basis of reception signals obtained by converting the reflection waves by the ultrasonic wave transducer elements; a fluid region calculation step of calculating a fluid region where the volume data satisfies a predetermined condition among the fluid in the subject body; a position calculation step of calculating a predetermined position in the fluid region; a sample marker position setting step of setting a position of a sample marker to the predetermined position calculated in a process of the position calculation step; a sample marker movement control step of controlling a movement of the position of the sample marker on the basis of sample marker position setting data set in a process of the sample marker position setting step; and a transmission and reception control step of performing a control such that ultrasonic waves are transmitted and received at the position of the sample marker whose movement is controlled in a process of the sample marker movement control step.

In order to solve the above-mentioned problems, an control processing program for an ultrasonic diagnostic apparatus according to an aspect of the present invention for causing a computer to execute a volume data generation step of oscillating a plurality of ultrasonic wave transducer elements to transmit ultrasonic waves and to receive reflection waves which are reflected from a subject body and generating volume data related to a fluid inside the subject body on the basis of reception signals obtained by converting the reflection waves by the ultrasonic wave transducer elements; a fluid region calculation step of calculating a fluid region where the volume data satisfies a predetermined condition among the fluid in the subject body; a position calculation step of calculating a predetermined position in the fluid region; a sample marker position setting step of setting a position of a sample marker to the predetermined position calculated in a process of the position calculation step; a sample marker movement control step of controlling a movement of the position of the sample marker on the basis of sample marker position setting data set in a process of the sample marker position setting step; and a transmission and reception control step of performing a control such that ultrasonic waves are transmitted and received at the position of the sample marker whose movement is controlled in a process of the sample marker movement control step.

In the ultrasonic diagnostic apparatus according to the present invention, the plurality of ultrasonic wave transducer elements are oscillated to transmit the ultrasonic waves and to receive the reflection waves which are reflected from the subject body and the volume data related to the fluid inside the subject body is generated on the basis of the reception signals obtained by converting the reflection waves by the ultrasonic wave transducer elements, the fluid region where the volume data satisfies the predetermined condition among the fluid in the subject body is calculated, the predetermined position is calculated in the fluid region; the position of the sample marker is set to the calculated predetermined position, the movement of the position of the sample marker is controlled on the basis of the set sample marker position setting data, and the control is performed such that the ultrasonic waves are transmitted and received at the position of the sample marker whose movement is controlled.

In the ultrasonic diagnostic method according to the present invention, the plurality of ultrasonic wave transducer elements are oscillated to transmit the ultrasonic waves and to receive the reflection waves which are reflected from the subject body and the volume data related to the fluid inside the subject body is generated on the basis of the reception signals obtained by converting the reflection waves by the ultrasonic wave transducer elements, the fluid region where the volume data satisfies the predetermined condition among the fluid in the subject body is calculated, the predetermined position is calculated in the fluid region; the position of the sample marker is set to the calculated predetermined position, the movement of the position of the sample marker is controlled on the basis of the set sample marker position setting data, and the control is performed such that the ultrasonic waves are transmitted and received at the position of the sample marker whose movement is controlled.

In the control process program for an ultrasonic diagnostic apparatus according to the present invention, the plurality of ultrasonic wave transducer elements are oscillated to transmit the ultrasonic waves and to receive the reflection waves which are reflected from the subject body and the volume data related to the fluid inside the subject body is generated on the basis of the reception signals obtained by converting the reflection waves by the ultrasonic wave transducer elements, the fluid region where the volume data satisfies the predetermined condition among the fluid in the subject body is calculated, the predetermined position is calculated in the fluid region; the position of the sample marker is set to the calculated predetermined position, the movement of the position of the sample marker is controlled on the basis of the set sample marker position setting data, and the control is performed such that the ultrasonic waves are transmitted and received at the position of the sample marker whose movement is controlled.

The nature and further characteristic features of the present invention will be made more clear from the following descriptions made with reference to the accompanying drawings.

BRIEF DESCRIPTION OF THE DRAWINGS

In the accompanying drawings:

FIG. 13 is an explanatory diagram for describing a movement method for the Doppler sample marker displayed on the display unit of FIG. 1;

FIG. 14 is an explanatory diagram for describing a Doppler angle correction factor calculation method in a Doppler angle correction factor calculation unit of FIG. 2;

FIG. 15 is an explanatory diagram for describing a case where a plurality of blood vessels are present in a region of interest for a tracking control displayed on the display unit of FIG. 1;

FIGS. 16A and 16B are explanatory diagrams for describing an input method for data related to a Doppler sample marker movement range;

DESCRIPTION OF THE PREFERRED EMBODIMENTS

Hereinafter, embodiments of the present invention will be described with reference to the drawings.

First Embodiment

Figure 1:
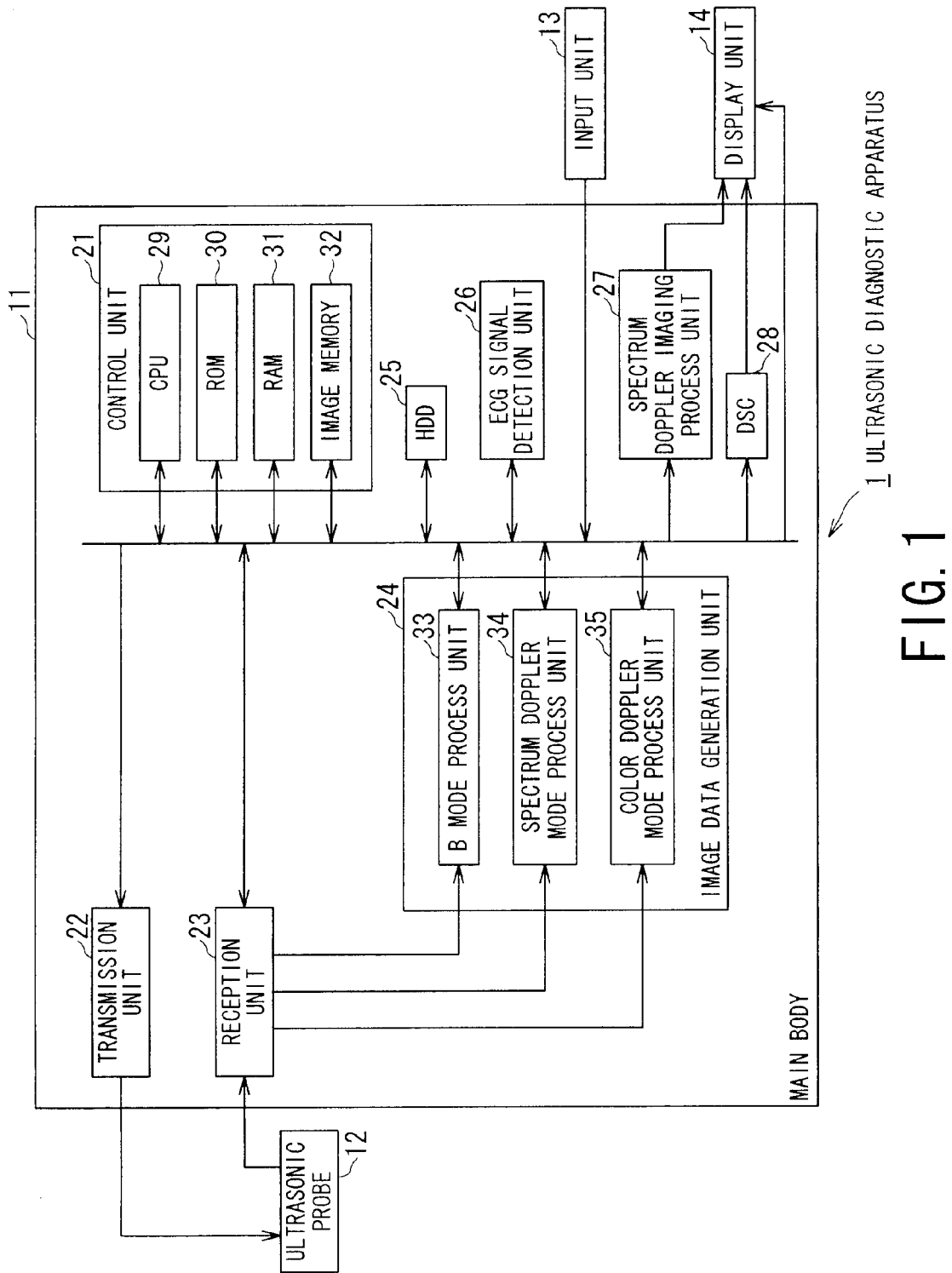
FIG. 1 is a block diagram illustrating an internal configuration of an ultrasonic diagnostic apparatus according to the present invention.

FIG. 1 illustrates an internal configuration of an ultrasonic diagnostic apparatus 1 according to the present invention.

The ultrasonic diagnostic apparatus 1 is composed of a main body 11, and an ultrasonic probe 12 connected to the main body 11 via an electronic cable (not shown), an input unit 13, and a display unit 14.

As illustrated in FIG. 1, the main body 11 of the ultrasonic diagnostic apparatus 1 is composed of a control unit 21, a transmission unit 22, a reception unit 23, an image data generation unit 24, an HDD (Hard Disc Drive) 25, an ECG signal detection unit 26, a spectrum Doppler imaging process unit 27, and a DSC (Digital Scan Converter) 28.

It should be noted that the control unit 21, the transmission unit 22, the reception unit 23, the image data generation unit 24, the HDD (Hard Disc Drive) 25, the ECG signal detection unit 26, the spectrum Doppler imaging process unit 27, and the DSC 28 are mutually connected via a bus in the main body 11 of the ultrasonic diagnostic apparatus 1.

The control unit 21 is composed of a CPU (Central Processing Unit) 29, a ROM (Read Only Memory) 30, a RAM (Random Access Memory) 31, an image memory 32, and the like. The CPU 29 executes various processes in accordance with programs stored in the ROM 30 or various application programs loaded from the HDD 25 to the RAM 31. Also, the CPU 29 generates various control signals and supplies the signals to the respective units, thus controlling the drive of the ultrasonic diagnostic apparatus 1 in an overall manner.

In addition, the RAM 31 appropriately stores necessary data for the CPU 29 to execute various processes, etc. The image memory 32 obtains B mode image data, spectrum Doppler mode image data, and color Doppler mode image data supplied from the image data generation unit 24 and stores the B mode image data, the spectrum Doppler mode image data, and the color Doppler mode image data thus obtained. As a result, for example, after the diagnosis, the operator makes the ultrasonic diagnostic apparatus 1 be capable to read the image data stored during the diagnosis and display the data via the DSC 28 on the display unit 14 as a still image or a moving image.

Also, the image memory 32 appropriately stores various image data such as raw data like an output signal (RF signal) supplied from the reception unit 23, image data obtained via a network (not shown), and the like, and supplies the data to the respective units when necessary.

It should be noted that instead of the CPU 29, an MPU (Micro Processing Unit) or the like may be used.

The transmission unit 22 is composed of a rate pulse generator, a transmission delay circuit, and a pulsar (each of which is not shown in the drawing). The rate pulse generator generates, on the basis of the control signal supplied from the control unit 21, a rate pulse for determining a pulse repeating frequency of an ultrasonic wave entering the inside of the subject body and supplies the rate pulse to the transmission delay circuit. Also, the transmission delay circuit is a delay circuit for setting a focal position and a deflection angle of an ultrasonic beam at the time of the transmission, and on the basis of the control signal supplied from the control unit 21, adding a delay time to the rate pulse supplied from the rate pulse generator so that the focal position and the deflection angle of the ultrasonic beam at the time of the transmission become a predetermined focal position and a predetermined deflection angle, before being supplied to the pulsar. Furthermore, the pulsar is a driver circuit for generating a high pressure pulse that is used for driving the ultrasonic wave transducer element. The pulsar generates high pressure pulse for driving the ultrasonic wave transducer element on the basis of the rate pulse supplied from the transmission delay circuit and outputs the thus generated high pressure pulse to the ultrasonic probe 12.

It should be noted that the transmission unit 22 can instantly change the delay time added to the rate pulse, the transmission frequency, the transmission drive voltage, and the like in accordance with the instructions from the control unit 21. In particular, in order that the transmission drive voltage can be instantly changed, the transmission unit 22 is provided, for example, with a linear amplifier type oscillating circuit, a circuit where a plurality of power source units are electrically switched over, or the like.

The reception unit 23 is composed of a preamplifier, an A/D converter, a reception delay circuit, and an adder (each of which is not shown in the drawing), etc. The preamplifier obtains a reception signal based on a reflection pulse of an ultrasonic pulse entering the subject body from the ultrasonic probe 12, amplifies the thus obtained reception signal to a predetermined level, and supplies the amplified reception signal to the A/D converter. The A/D converter converts the reception signal supplied from the preamplifier from an analog signal to a digital signal and supplies the signal to the reception delay circuit.

On the basis of the control signal supplied from the control unit 21, the reception delay circuit gives a delay time (a delay time corresponding to a difference in ultrasonic wave propagation times from the focal positions of the respective ultrasonic wave transducers) necessary for determining a reception directivity to the reception signal after the A/D conversion that is supplied from the A/D converter, and the signal has been supplied to the adder. The adder adds the reception signals from the respective ultrasonic wave transducers which are supplied from the reception delay circuit and supplies the added reception signal to the image data generation unit 24. It should be noted that due to the addition of the adder, a reflection component from the direction corresponding to the reception directivity of the reception signal is emphasized.

The image data generation unit 24 is composed of a B mode process unit 33, a spectrum Doppler mode process unit 34, and a color Doppler mode process unit 35. The B mode process unit 33 is composed of a logarithmic amplifier, an envelope detection circuit, a TGC (Time Gain Control) circuit (each of which is not shown in the drawing), and the like, and performs the following process on the basis of the control signal supplied from the control unit 21.

That is, the logarithmic amplifier of the B mode process unit 33 performs a logarithmic amplification on the reception signal supplied from the reception unit 23 and supplies the reception signal after the logarithmic amplification to the envelope detection circuit. The envelope detection circuit is a circuit for detecting only an amplitude by removing the ultrasonic frequency components. The envelope detection circuit then detects an envelop about the reception signal supplied from the logarithmic amplifier and supplies the detected reception signal to a TGC circuit. The TGC circuit adjusts an intensity of the reception signal supplied from the envelope detection circuit so that a luminance of the final image becomes uniform and supplies the adjusted B mode image data to the image memory 32 or the HDD 25 of the control unit 21. The B mode image data stored in the image memory 32 or the HDD 25 of the control unit 21 is supplied via the DSC 28 to the display unit 14. After that, the data is displayed as a B mode image in which the intensity of the reception signal is represented on the basis of the luminance.

The spectrum Doppler mode process unit 34 is composed of a Doppler shift signal detector (not shown) for detecting a Doppler shift signal from the reception signal which is supplied from the reception unit 23, and an analysis unit (not shown) for analyzing a spectrum distribution of the Doppler shift signal detected by the Doppler shift signal detector.

The Doppler shift signal detector is composed of a reference signal generator, a $\Pi/2$ phase shifter, a mixer, an LPF (Low Pass Filter) (each of which is not shown in the drawing), and the like. The Doppler shift signal detector mainly performs an orthogonal phase detection or the like on the reception signal supplied from the reception unit 23 and supplies the detected Doppler shift signal to the analysis unit.

The analysis unit is composed of an FFT (Fast Fourier Transform) analyzer, a computation section, and the like. The FFT analyzer performs an FFT analysis on the Doppler shift signal supplied from the Doppler shift signal detector at a predetermined width with a predetermined depth corresponding to the position of the Doppler sample marker as the center. The computation section performs a computation such as a center frequency, the dispersion, or the like, with respect to the frequency spectrum from the FFT analyzer and supplies the spectrum Doppler mode image data generated from the computation to the image memory 32 or the HDD 25 of the control unit 21. The spectrum Doppler mode image data stored in the image memory 32 or the HDD 25 of the control unit 21 is supplied via the spectrum Doppler imaging process unit 27 to the display unit 14. After that, the spectrum Doppler mode image data is displayed as a spectrum Doppler mode image representing the distribution of the frequency spectrum included in the reception signal.

The color Doppler mode process unit 35 is composed of a Doppler shift signal detector (not shown) for detecting a Doppler shift signal from the reception signal supplied from the reception unit 23 and an extraction computation unit (not shown) for extracting blood flow information such as an average speed, a variance, and a power of the blood flow from the Doppler shift signal detected by the Doppler shift signal detector. It should be noted that the Doppler shift signal detector (not shown) of the color Doppler mode process unit 35 has a similar configuration to that of the Doppler shift signal detector (not shown) of the spectrum Doppler mode process unit 34, and a description thereof will be omitted to avoid a repetition.

The extraction computation unit is composed of an MTI filter (Moving Target Indication Filter), an autocorrelator, an average speed computation section, a variance computation section, a power computation section (each of which is not shown in the drawing), and the like. The MTI filter removes an unnecessary fixed reflection wave from a fixed reflection body (for example, a blood vessel wall, a cardiac wall, etc.) with respect to the Doppler shift signal supplied from the Doppler shift signal process unit and supplies the Doppler shift signal from which the fixed reflection wave is removed to the autocorrelator. The autocorrelator performs a frequency analysis at multiple points on the Doppler shift signal from which the fixed reflection wave is removed which is supplied from the MTI filter, before being supplied to the average speed computation section, the variance computation section, and the power computation section.

The average speed computation section, the variance computation section, and the power computation section respectively computes the average speed, the dispersion, and the power of the blood flow and supplies the color Doppler mode image data generated through the computation to the image memory 32 or the HDD 25 of the control unit 21. The color Doppler mode image data stored in the image memory 32 or the HDD 25 of the control unit 21 is supplied via the DSC 28 to the display unit 14, and after that, is displayed as a color Doppler mode image representing the blood flow information such as the average speed, the variance, and the power of the blood flow.

The HDD 25 stores various data groups related to control programs for executing a scan sequence, an image generation and display process, a difference image generation process, a luminance value holding computation process, an overlap display, and the like, diagnosis information (patient ID, findings of a doctor, etc.), a diagnosis protocol, ultrasonic wave transmission and reception conditions, a computation condition for a computation process, and other information. Also, the HDD 25 stores, if necessary, various pieces of image data supplied from the image memory 32 of the control unit 21. The HDD 25 can transfer various pieces of data, when necessary, to an external device (not shown) via an interface unit (not shown).

The ECG signal detection unit 26 is composed of a sensor which is mounted to a body surface of the subject body, for detection an ECG signal in accordance with the control of the control unit 21 and an A/D converter for converting the ECG signal detected by the sensor from an analog signal to a digital signal and supplies the ECG signal after the conversion to the image memory 32 or the HDD 25 of the control unit 21. This ECG signal is stored in the image memory 32 or the HDD 25 of the control unit 21 as additional information for the B mode image data, the color Doppler mode image data, and the like.

The spectrum Doppler imaging process unit 27 obtains the spectrum Doppler mode image data supplied from the image memory 32 of the control unit 21 and performs an imaging process such that the thus obtained spectrum Doppler mode image data can be displayed on the display unit 14 as a spectrum of the temporal change in the Doppler shift frequency (speed) and supplied to the display unit 14.

The DSC 28 reads the B mode image data, the color Doppler mode image data, the ECG signal, etc., supplied from the image memory 32 of the control unit 21 and converts the B mode image data, the color Doppler mode image data, the ECG signal etc., thus read, into a scanning line signal sequence in a video format from a scanning line signal sequence of the ultrasonic wave scan. The DSC 28 subjects the resultant to a predetermined image processing and a calculation processing to be supplied to the display unit 15.

Also, the ultrasonic probe 12 is connected to the main body 11 via an electronic cable (not shown). The ultrasonic probe 12 is an ultrasonic transducer for performing transmission and reception for the ultrasonic wave by contacting its front surface with the surface of the subject. The ultrasonic probe 12 has minute ultrasonic wave transducer elements arranged in an array in a one dimensional manner or in a matrix in a two dimensional manner at its distal end part. This ultrasonic wave transducer element is an electro-acoustic transducer element as a piezoelectric vibrator. A matching layer for efficiently propagating the ultrasonic wave is provided on a front side of the ultrasonic wave transducer element, and a packing material for preventing the propagation of the ultrasonic wave is provided on a back side thereof.

The ultrasonic probe 12 converts an electric pulse incident on the transmission unit 22 of the main body 11 into an ultrasonic pulse (transmission ultrasonic wave) at the time of transmission and also converts a reflection wave reflected by the subject body into an electric signal at the time of reception, before being output to the main body 11. It should be noted that a part of the ultrasonic wave transmitted to the inside of the subject body is reflected by a boundary surface between organs inside the subject body or tissues having different acoustic impedances. Also, when the transmitted ultrasonic wave is reflected by a moving blood flow, a front surface of the cardiac wall, or the like, the transmitted ultrasonic wave is subjected to the frequency shift due to the Doppler effect.

The input unit 13 is connected to the main body 11 via the electric cable. The input unit 13 has a display panel (not shown) for inputting various instructions of the operator on an operation panel and input devices such as a track ball, various operation switches, various buttons, a mouse, and a key board, which are used for the operator to input various data such as patient information, a measurement parameter, and a physical parameter.

The display unit 14 is connected to the spectrum Doppler imaging process unit 27 and the DSC 28 of the main body 11 via a cable and is provided with an LCD (Liquid Crystal Display) and a CRT (Cathode Ray Tube), which are not shown in the drawing. The display unit obtains the spectrum Doppler image data after the imaging process from the spectrum Doppler imaging process unit 27. Also, the display unit obtains the B mode image data, the color Doppler mode image data, the ECG signal, etc. from the DSC 28 that is converted from a scanning line signal sequence of the ultrasonic wave scan into a scanning line signal sequence in a video format, to display the spectrum Doppler image based on the thus obtained spectrum Doppler image data, the B mode image based on the thus obtained B mode image data, the color Doppler mode image based on the thus obtained color Doppler mode image data, and the like, on the LCD or the CRT (not shown) and to also display the ECG signal as additional information on the LCD or the CRT (not shown).

Figure 2:
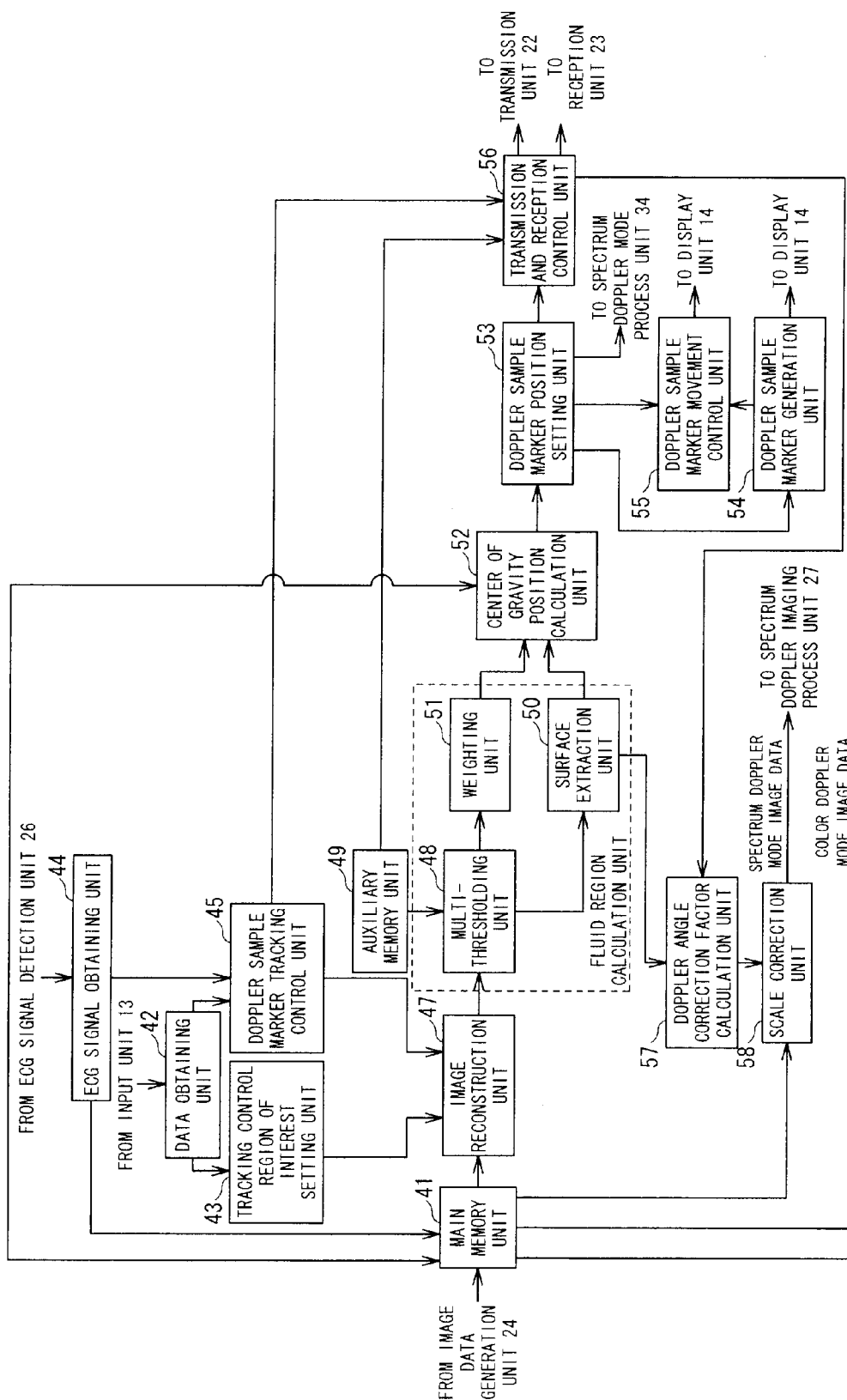
FIG. 2 is a block diagram illustrating a functional configuration executable by the ultrasonic diagnostic apparatus of FIG. 1 according to a first embodiment.

FIG. 2 is a block diagram illustrating a functional configuration executable by the ultrasonic diagnostic apparatus 1 of FIG. 1.

A main memory unit 41 is realized by the RAM 31 of FIG. 1, the image memory 32, or the like. The main memory unit 41 obtains the B mode image data, the spectrum Doppler image data, and the color Doppler mode image data supplied from the image data generation unit 24 and stores the B mode image data, the spectrum Doppler image data, and the color Doppler mode image data thus obtained. The main memory unit 41 obtains an ECG signal supplied from an ECG signal obtaining unit 44 and stores the thus obtained ECG signal. Also, the main memory unit 41 appropriately stores necessary data for the CPU 29 to execute various processes and supplies the stored data to the respective units.

A data obtaining unit 42 obtains various pieces of data that are input while the operator operates the input unit 13 and supplies the thus obtained various pieces of data to the respective units. In particular, when the operator operates a Doppler sample marker tracking start button (not shown) of the input unit 13, the data obtaining unit 42 obtains data related to an instruction indicating that a Doppler sample marker tracking control process is to be started. On the basis of the thus obtained data related to the instruction indicating that the Doppler sample marker tracking control process is to be started, the data obtaining unit 42 generates an instruction signal indicating that the Doppler sample marker tracking control process is to be started and supplies the signal to a Doppler sample marker tracking control unit 45.

Then, while the operator operates a Doppler sample marker tracking end button (not shown) of the input unit 13, when the data obtaining unit 42 obtains the data related to the instruction indicating that the Doppler sample marker tracking control process is to be ended, the data obtaining unit 42 generates an instruction signal indicating that the Doppler sample marker tracking control process is to be ended on the basis of the data related to the instruction indicating that the Doppler sample marker tracking control process is to be ended and supplies the signal to the Doppler sample marker tracking control unit 45.

A tracking control region of interest setting unit 43 obtains data related to a desired region of interest for tracking of the Doppler sample marker of the spectrum Doppler that is supplied from the data obtaining unit 42 and sets a tracking region of interest on the basis of the thus obtained data related to the tracking region of interest. Then, the tracking control region of interest setting unit 43 supplies tracking region of interest setting data that is data related to the set tracking region of interest to an image reconstruction unit 47.

The ECG signal obtaining unit 44 obtains the ECG signal supplied from the ECG signal detection unit 26 and supplies the thus obtained ECG signal to the main memory unit 41 and the Doppler sample marker tracking control unit 45.

The Doppler sample marker tracking control unit 45 determines whether or not the instruction signal indicating that the Doppler sample marker tracking control process is to be started, which is supplied from the data obtaining unit 42, is obtained. In a case where it is determined that the instruction signal indicating that the Doppler sample marker tracking control process is to be started is obtained, the Doppler sample marker tracking control unit starts the Doppler sample marker tracking control process.

The Doppler sample marker tracking control unit 45 obtains the ECG signal supplied from the ECG signal obtaining unit 44. On the basis of the thus obtained ECG signal, the Doppler sample marker tracking control unit 45 determines whether or not the heart of the subject body is in a diastole phase. In a case where it is determined that the heart of the subject body is in the diastole phase, the Doppler sample marker tracking control unit 45 executes the Doppler sample marker tracking control process for the diastole phase of the heart. On the other hand, in a case where it is determined that the heart of the subject body is in a systolic phase, the Doppler sample marker tracking control unit executes the Doppler sample marker tracking control process for the systolic phase of the heart.

Also, the Doppler sample marker tracking control unit 45 determines whether or not the instruction signal indicating that the Doppler sample marker tracking control process is to be ended, which is supplied from the data obtaining unit 42, is obtained. In a case where it is determined that the instruction signal indicating that the Doppler sample marker tracking control process is to be ended, is obtained, the Doppler sample marker tracking control unit ends the Doppler sample marker tracking control process.

A Doppler sample marker movement range setting unit 46 obtains data related to a Doppler sample marker movement range of the spectrum Doppler which is supplied from the data obtaining unit 42 (that is, data related to a range where a movement restriction of the Doppler sample marker is desired by the operator). On the basis of the data related to the Doppler sample marker movement range, the Doppler sample marker movement range setting unit 46 sets the movement range of the Doppler sample marker and supplies Doppler sample marker movement range set data that is data related to the thus set Doppler sample marker movement range to the image reconstruction unit 47.

The image reconstruction unit 47 reads out the plurality of pieces of two dimensional color Doppler mode image data supplied from the main memory unit 41. The image reconstruction unit converts the thus read plurality of pieces of two dimensional color Doppler mode image data into volume data having a common coordinate axis and also supplies the volume data after the conversion to the main memory unit 41. It should be noted that the volume data after the conversion include volume data of an average speed of blood flow (hereinafter referred to as "blood flow speed"), volume data of a power (signal intensity), and the like.

The image reconstruction unit 47 generates, on the basis of the volume data after the conversion, three dimensional color Doppler mode image data through reconstruction with use of a predetermined computation process and supplies the thus generated three dimensional color Doppler mode image data to the main memory unit 41.

Also, the image reconstruction unit 47 reads, in accordance with the control of the Doppler sample marker tracking control unit 45, the volume data of the blood flow speed stored in the main memory unit 41 and supplies the read volume data of the blood flow speed to a multi-thresholding unit 48 of a fluid region computation unit. It should be noted that the fluid region computation unit is composed of the multi-thresholding unit 48, a surface extraction unit 50, a weighting unit 51, and the like.

The multi-thresholding unit 48 obtains the volume data of the blood flow speed that is supplied from the image reconstruction unit 47. The multi-thresholding unit 48 reads out a reference value related to a blood flow speed for performing a multi-thresholding process, which is previously stored in an auxiliary memory unit 49 composed of the HDD 25 or the like. On the basis of the read reference value related to the blood flow speed, the multi-thresholding unit 48 performs the multi-thresholding process on the thus obtained volume data of the blood flow speed and supplies the multi-threshold volume data that is volume data after the multi-thresholding to the surface extraction unit 50 and the weighting unit 51.

The surface extraction unit 50 obtains the multi-threshold volume data supplied from the multi-thresholding unit 48. On the basis of the thus obtained multi-threshold volume data, the surface extraction unit 50 extracts a surface of the blood flow and supplies blood flow surface extraction data that is data related to the extracted blood flow surface to a center of gravity position calculation unit 52.

The weighting unit 51 obtains the multi-threshold volume data supplied from the multi-thresholding unit 48. On the basis of the thus obtained multi-threshold volume data, the weighting unit 51 produces a weighting used when a position of the center of gravity in a blood flow region that is formed by the blood flow surface (a fluid region where the multi-threshold volume data satisfies a predetermined condition among the fluid of the subject body) in the center of gravity position calculation unit 52 and supplies the weighting result to the center of gravity position calculation unit 52.

The center of gravity position calculation unit 52 obtains the multi-threshold volume data supplied from the surface extraction unit 50 and also obtains the weighting result supplied from the weighting unit 51. On the basis of the multi-threshold volume data and the weighting result thus obtained, the center of gravity position calculation unit 52 calculates the position of the center of gravity of the blood flow region formed by the blood flow surface and supplies center of gravity calculation data, which is the calculation result, to the main memory unit 41 and a Doppler sample marker position setting unit 53.

The Doppler sample marker position setting unit 53 obtains the center of gravity position calculation data supplied from the center of gravity position calculation unit 52. On the basis of the thus obtained center of gravity position calculation data, the Doppler sample marker position setting unit 53 sets the position of the Doppler sample marker at the position of the center of gravity for the calculated blood flow region, and supplies Doppler sample marker position setting data that is data related to the set position of the Doppler sample marker to the spectrum Doppler mode process unit 34, a Doppler sample marker generation unit 54, a Doppler sample marker movement control unit 55, and a transmission and reception control unit 56.

The Doppler sample marker generation unit 54 obtains the Doppler sample marker position setting data supplied from the Doppler sample marker position setting unit 53. On the basis of the thus obtained Doppler sample marker position setting data, the Doppler sample marker generation unit 54 generates a Doppler sample marker having a predetermined width at a position which is set in advance, and supplies Doppler sample marker generation data that is data related to the thus generated Doppler sample marker to the display unit 14.

The Doppler sample marker movement control unit 55 obtains the Doppler sample marker position setting data supplied from the Doppler sample marker position setting unit 53. On the basis of the thus obtained Doppler sample marker position setting data, the Doppler sample marker movement control unit 55 generates a Doppler sample marker movement control signal for controlling the movement of the Doppler sample marker already displayed on the display unit 14 and supplies the signal to the display unit 14.

A transmission and reception control unit 56 reads the scan sequence, conditions for transmitting and receiving the ultrasonic waves, etc., previously stored in the auxiliary memory unit 49. On the basis of the thus read scan sequence, conditions for transmitting and receiving the ultrasonic waves, etc., the transmission and reception control unit 56 generates a transmission control signal and a reception control signal for controlling the transmission and reception of the ultrasonic waves in a case where the B mode image data and the color Doppler mode image data are generated and supplies the transmission control signal and the reception control signal thus generated to the transmission unit 22 and the reception unit 23, respectively.

In addition, the transmission and reception control unit 56 obtains the Doppler sample marker position setting data supplied from the Doppler sample marker position setting unit 53. On the basis of the thus obtained Doppler sample marker position setting data, in a case where the spectrum Doppler mode image data is generated, the transmission and reception control unit 56 generates a transmission control signal and a reception control signal for transmitting and receiving the ultrasonic waves on a scanning line including the set position of the Doppler sample marker and supplies the transmission control signal and the reception control signal thus generated to the transmission unit 22 and the reception unit 23, respectively.

The transmission and reception control unit 56 supplies ultrasonic beam direction data that is data related to an ultrasonic beam direction in which the ultrasonic waves are transmitted and received on the scanning line including the set position of the Doppler sample marker to a Doppler angle correction factor calculation unit 57.

The Doppler angle correction factor calculation unit 57 obtains the blood flow surface extraction data supplied from the surface extraction unit 50 and also obtains the ultrasonic beam direction data supplied from the transmission and reception control unit 56. On the basis of the blood flow surface extraction data and the ultrasonic beam direction data thus obtained, the Doppler angle correction factor calculation unit 57 calculates an angle defined by the longitudinal direction in the blood flow region and the ultrasonic beam direction. The Doppler angle correction factor calculation unit 57 calculates, with use of the calculated angle, an angle correction factor for setting an accurate blood flow speed, which is to be multiplied to the spectrum Doppler mode image data, and supplies angle correction factor data that is data related to the calculated angle correction factor to a scale correction unit 58.

The scale correction unit 58 reads the spectrum Doppler mode image data stored in the main memory unit 41 and also obtains the angle correction factor data supplied from the Doppler angle correction factor calculation unit 57. The scale correction unit 58 corrects the scale by multiplying the thus read spectrum Doppler mode image data by the angle correction factor and supplies the spectrum Doppler image data after the correction to the spectrum Doppler imaging process unit 27.

With reference to flowcharts of FIGS. 3 and 4, a Doppler sample marker tracking control process of the ultrasonic diagnostic apparatus 1 in FIG. 2 will be described.

In Step S1, the Doppler sample marker tracking control unit 45 determines whether or not the instruction signal indicating that the Doppler sample marker tracking control process is to be started, which is supplied from the data obtaining unit 42, is obtained, and stands by until it is determined that the instruction signal indicating that the Doppler sample marker tracking control process is to be started is obtained.

That is, when the operator operates a Doppler sample marker tracking start button (not shown) of the input unit 13, the data obtaining unit 42 obtains the data related to the instruction indicating that the Doppler sample marker tracking control process is started, the data obtaining unit 42 generates the instruction signal indicating that the Doppler sample marker tracking control process is to be started on the basis of the thus obtained data related to the instruction indicating that the Doppler sample marker tracking control process is started and supplies the signal to the Doppler sample marker tracking control unit 45.

The Doppler sample marker tracking control unit 45 determines whether or not the instruction signal indicating that the Doppler sample marker tracking control process is to be started, which is supplied from the data obtaining unit 42, is obtained, and stands by until it is determined that the instruction signal indicating that the Doppler sample marker tracking control process is to be started is obtained.

In Step S1, if it is determined that the instruction signal indicating that the Doppler sample marker tracking control process is to be started is obtained, the Doppler sample marker tracking control unit 45 starts the Doppler sample marker tracking control process in Step S2. That is, the Doppler sample marker tracking control unit 45 controls the transmission and reception control unit 56 and generates the transmission control signal and the reception control signal for generating the two dimensional B mode image data and the plurality of pieces of two dimensional color Doppler mode image data.

In accordance with the control of the Doppler sample marker tracking control unit 45, the transmission and reception control unit 56 generates the transmission control signal and the reception control signal for generating the two dimensional B mode image data and the plurality of pieces of two dimensional color Doppler mode image data and supplies the signals to the transmission unit 22 and the reception unit 23, respectively.

In Step S3, the B mode process unit 33 of the image data generation unit 24 generates the two dimensional B mode image data. That is, the following process will be performed.

The transmission unit 22 transmits an ultrasonic beam for generating the B mode image data to the subject body on the basis of the transmission control signal supplied from the transmission and reception control unit 56. That is, a rate pulsar of the transmission unit 22 generates a rate pulse for setting a pulse repetition frequency of the ultrasonic pulse entering the inside of the subject body as a predetermined pulse repetition frequency on the basis of the transmission control signal supplied from the transmission and reception control unit 56, and supplies the rate pulse to the transmission delay circuit. Then, the transmission delay circuit adds, on the basis of the transmission control signal supplied from the transmission and reception control unit 56, a delay time to the rate pulse supplied from the rate pulse generator so that the focal position and the deflection angle of the ultrasonic beam at the time of the transmission become a predetermined focal position and a predetermined deflection angle ($\theta1$), before being supplied to the pulsar. Furthermore, the pulsar generates a high pressure pulse for driving the ultrasonic wave transducer on the basis of the rate pulse supplied from the transmission delay circuit and outputs the thus generated high pressure pulse to the ultrasonic probe 12. The ultrasonic probe 12 converts the high pressure pulse that is input from the transmission unit 22 into a high pressure pulse (electric pulse) and transmits the converted ultrasonic pulse to the subject body. A part of the ultrasonic wave transmitted to the inside of the subject body is reflected by a boundary surface between organs inside the subject body or tissues having different acoustic impedances.

The ultrasonic probe 12 converts the reflected wave reflected by the subject body into an electric signal and outputs the electric signal to the main body 11. The reception unit 23 amplifies the reception signal input from the ultrasonic probe 12 on the basis of the reception control signal supplied from the transmission and reception control unit 56 and adds a predetermined delay time to the signal, before being supplied to the B mode process unit 33 of the image data generation unit 24. That is, the preamplifier of the reception unit 23 obtains a reception signal based on a reflection pulse of an ultrasonic pulse entering the subject body from the ultrasonic probe 12, amplifies the thus obtained reception signal to a predetermined level, and supplies the amplified reception signal to the A/D converter. The A/D converter converts the reception signal supplied from the preamplifier from an analog signal to a digital signal and supplies the signal to the reception delay circuit.

The reception delay circuit adds, on the basis of the reception control signal supplied from the transmission and reception control unit 56, a delay time (a delay time corresponding to a difference in ultrasonic wave propagation times from the focal positions of the respective ultrasonic wave transducers) necessary for determining a reception directivity, to the reception signal after the A/D conversion that has been supplied from the A/D converter before being supplied to the adder. The adder adds the reception signals from the respective ultrasonic wave transducers which are supplied from the reception delay circuit and supplies the added reception signal to the B mode process unit 33.

The B mode process unit 33 performs various processes on the reception signal supplied from the reception unit 23 and respectively generates the B mode image data in a $\theta1$ direction, before being supplied to the main memory unit 41. The main memory unit 41 obtains the B mode image data in the $\theta1$ direction supplied from the B mode process unit 33 and stores the thus obtained B mode image data in the $\theta1$ direction.

Next, the transmission and reception direction of the ultrasonic wave is sequentially updated by $\Delta\theta$ to change up to $[\theta1+(N-1)\Delta\theta]$, and the transmission and reception of the ultrasonic waves is performed through the N direction scanning in the similar procedure as described above to scan the subject body in real time. At this time, in response to the control signal, the transmission and reception control unit 56 sequentially switches the delay times of the transmission delay circuit and the reception delay circuit in the transmission unit 22 and the reception unit 23, respectively while corresponding to the predetermined ultrasonic wave transmission and reception direction to generate the respective B mode image data in $[\theta1+\Delta\theta]$ to $[\theta1+(N-1)\Delta\theta]$ directions.

Also, the main memory unit 41 stores the thus generated B mode image data in the $[\theta1+\Delta\theta]$ to $[\theta1+(N-1)\Delta\theta]$ directions together with the previously stored B mode image data in the $\theta1$ direction as two dimensional B mode image data at a predetermined time phase.

In Step S4, the color Doppler mode process unit 35 of the image data generation unit 24 generates a plurality of pieces of two dimensional color Doppler mode image data. That is, the following process will be performed.

The transmission unit 22 transmits, on the basis of the transmission control signal supplied from the transmission and reception control unit 56, an ultrasonic beam for generating the color Doppler mode image data to the subject body. That is, the rate pulsar of the transmission unit 22 generates, on the basis of the transmission control signal supplied from the transmission and reception control unit 56, a rate pulse for setting a pulse repetition frequency of the ultrasonic pulse entering the inside of the subject body as a predetermined pulse repetition frequency and supplies the rate pulse to the transmission delay circuit. Then, the transmission delay circuit adds, on the basis of the transmission control signal supplied from the transmission and reception control unit 56, a delay time to the rate pulse supplied from the rate pulse generator so that the focal position and the deflection angle of the ultrasonic beam at the time of the transmission become a predetermined focal position and a predetermined deflection angle ($\theta1$), before being supplied to the pulsar. Furthermore, the pulsar generates a high pressure pulse for driving the ultrasonic wave transducer on the basis of the rate pulse supplied from the transmission delay circuit and outputs the thus generated high pressure pulse to the ultrasonic probe 12. The ultrasonic probe 12 converts the high pressure pulse that is input from the transmission unit 22 into a high pressure pulse (electric pulse) and transmits the converted ultrasonic pulse to the subject body. A part of the ultrasonic wave transmitted to the inside of the subject body is reflected by a boundary surface between organs inside the subject body or tissues having different acoustic impedances.

The ultrasonic probe 12 converts a reflection wave reflected by the subject body into an electric signal and outputs the electric signal to the main body 11. The reception unit 23 amplifies, on the basis of the reception control signal supplied from the transmission and reception control unit 56, the reception signal input from the ultrasonic probe 12, adds a predetermined time, and supplies the signal to the color Doppler mode process unit 35 of the image data generation unit 24. That is, the preamplifier of the reception unit 23 obtains a reception signal based on a reflection pulse of an ultrasonic pulse entering the subject body from the ultrasonic probe 12, amplifies the thus obtained reception signal to a predetermined level, and supplies the amplified reception signal to the A/D converter. The A/D converter converts the reception signal supplied from the preamplifier from an analog signal to a digital signal and supplies the signal to the reception delay circuit.

On the basis of the reception control signal supplied from the transmission and reception control unit 56, the reception delay circuit gives a delay time (a delay time corresponding to a difference in ultrasonic wave propagation times from the focal positions of the respective ultrasonic wave transducers) necessary for determining a reception directivity to the reception signal after the A/D conversion that has been supplied from the A/D converter, and the signal is supplied to the adder. The adder adds the reception signals from the respective ultrasonic wave transducers which are supplied from the reception delay circuit and supplies the added reception signal to the color Doppler mode process unit 35.

After that, in order to generate the color Doppler mode image data, the transmission and reception of the ultrasonic waves are repeated on the same scanning line by a predetermined times.

The Doppler shift signal detector of the color Doppler mode process unit 35 supplies the Doppler shift signal detected when the reception signal supplied from the reception unit 23 is mainly subjected to orthogonal phase detection or the like, to the extraction computation unit.

The MTI filter of the extraction computation unit removes an unnecessary fixed reflection wave from a fixed reflection body with respect to the Doppler shift signal supplied from the Doppler shift signal detector and supplies the Doppler shift signal from which the fixed reflection wave is removed to the autocorrelator. The autocorrelator performs a frequency analysis at multiple points on the Doppler shift signal from which the fixed reflection wave is removed which is supplied from the MTI filter, before being supplied to the average speed computation section, the variance computation section, and the power computation section.

The average speed computation section, the variance computation section, and the power computation section respectively compute the average speed, the dispersion, and the power of the blood flow, and supply the color Doppler mode image data generated through the computation to the main memory unit 41 in the θ1 direction. The main memory unit 41 obtains the color Doppler mode image data in the θ1 direction supplied from the color Doppler mode process unit 35 and stores the thus obtained color Doppler mode image data in the θ1 direction.

Next, the transmission and reception direction of the ultrasonic wave is sequentially updated by Δθ to change up to [θ1+(N−1)Δθ] and the transmission and reception of the ultrasonic waves is performed through the N direction scanning in the similar procedure as described above to scan the subject body in real time. At this time, in response to the control signal, the transmission and reception control unit 56 sequentially switches the delay times of the transmission delay circuit and the reception delay circuit in the transmission unit 22 and the reception unit 23, respectively while corresponding to the predetermined ultrasonic wave transmission and reception direction, and generates the respective color Doppler mode image data in the [θ1+Δθ] to [θ1+(N−1)Δθ] directions.

Also, the main memory unit 41 stores the color Doppler mode image data generated in the [θ1+Δθ] to [θ1+(N−1)Δθ] directions together with the previously stored color Doppler mode image data in the θ1 direction, as the two dimensional color Doppler mode image data at a predetermined time phase.

In this manner, it is possible to generate and store the one sheet of the two color Doppler mode image data in the predetermined time phase.

It should be noted that according to the embodiment of the present invention, after the transmission and reception of the ultrasonic waves are performed on the same scanning line by plural times, sequentially, the transmission and reception of the ultrasonic waves performed on another scanning line by plural times to generate the color Doppler mode image data. However, the present invention is not limited to such a case and may be applied to a case where the color Doppler mode image data is generated through another scanning method.

Next, a plurality of pieces of two dimensional color Doppler mode image data are generated across a three dimensional region through the similar operation under different spatial conditions.

To be more specific, when the manual scanning by the operator is performed with use of the ultrasonic probe 12 which has the plurality of ultrasonic wave transducer elements arranged in an array in a one dimensional manner, for example, a mechanical scanning, a parallel movement scanning, or the like is manually performed at a given speed, the tomographic image data across the three dimensional region composed of the plurality of pieces of two dimensional tomographic image data is collected. It is needless to mention that a scanning with use of the ultrasonic probe 12 which has the plurality of ultrasonic wave transducer elements arranged in an array in a one dimensional manner may be performed in a mechanical manner.

Also, the tomographic image data across the three dimensional region may be collected through a direct three dimensional scanning with use of the ultrasonic probe 12 which has the plurality of ultrasonic wave transducer elements arranged in a matrix in a two dimensional manner. According to the present invention, it suffices as long as the tomographic image data across the three dimensional region can be collected. The present invention may also be applied to cases where the tomographic image data across the three dimensional region is collected through any scanning method.

The plurality of thus generated pieces of two dimensional color Doppler mode image data are sequentially stored in the main memory unit 41.

It should be noted that through the processes in Steps S3 and S4, when the two dimensional B mode image data and a plurality of pieces of two dimensional color Doppler mode image data are generated, the ECG signal detection unit 26 detects the ECG signal from the subject body and supplies the detected ECG signal to the ECG signal obtaining unit 44. The ECG signal obtaining unit 44 obtains the ECG signal supplied from the ECG signal detection unit 26 and supplies the thus obtained ECG signal to the main memory unit 41 and the Doppler sample marker tracking control unit 45.

The main memory unit 41 obtains the ECG signal supplied from the ECG signal obtaining unit 44 and stores the thus obtained ECG signal as additional information for the previously stored B mode image data, color Doppler mode image data, and the like.

In Step S5, the image reconstruction unit 47 reads the plurality of pieces of two dimensional color Doppler mode image data stored in the main memory unit 41 and converts the thus read plurality of pieces of two dimensional color Doppler mode image data into volume data having a common coordinate axis, before being supplied to the main memory unit 41. The main memory unit 41 obtains the volume data supplied from the image reconstruction unit 47 and stores the thus obtained volume data. It should be noted that the volume data after the conversion includes the volume data of the blood flow speed, power (signal intensity), etc.

In Step S6, on the basis of the volume data after the conversion, the image reconstruction unit 47 generates three dimensional color Doppler mode image data through reconstruction with use of a predetermined computation process and supplies the thus generated three dimensional color Doppler mode image data to the main memory unit 41.

The main memory unit 41 obtains the three dimensional color Doppler mode image data supplied from the image reconstruction unit 47 and stores the thus obtained three dimensional color Doppler mode image data.

The DSC 28 reads the two dimensional B mode image data, the three dimensional color Doppler mode image data, and the ECG signal from the main memory unit 41 and converts the two dimensional B mode image data, the three dimensional color Doppler mode image data, and the ECG signal thus read into a scanning line signal sequence in a video format from a scanning line signal sequence of the ultrasonic wave scan. The signal is signal sequence is subjected to a predetermined image process or a computation process and is then supplied to the display unit 14.

In Step S7, the display unit 14 obtains the two dimensional B mode image data, the three dimensional color Doppler mode image data, and the ECG signal, which are converted into the scanning line signal sequence in the video format from the scanning line signal sequence of the ultrasonic wave scan from the DSC 28. The display unit 14 displays a two dimensional B mode image based on the thus obtained two dimensional B mode image data and a three dimensional color Doppler image based on the three dimensional color Doppler mode image data on the CRT or LCD (not shown) while being overlapped, and also displays the ECG signal as the additional information on the CRT or the LCD (not shown).

It should be noted that according to the embodiment of the present invention, the two dimensional B mode image based on the two dimensional B mode image data and the three dimensional color Doppler image based on the three dimensional color Doppler mode image data while being overlapped, but for example, a three dimensional B mode image and a three dimensional color Doppler image may be displayed while being overlapped.

Next, the operator operates the input unit 13 while referring to the two dimensional B mode image based on the two dimensional B mode image data and the three dimensional color Doppler image based on the three dimensional color Doppler mode image data displayed on the display unit 14 to input data related to a three dimensional tracking control region of interest where the tracking of the Doppler sample marker of the spectrum Doppler is desired.

Figure 5A:
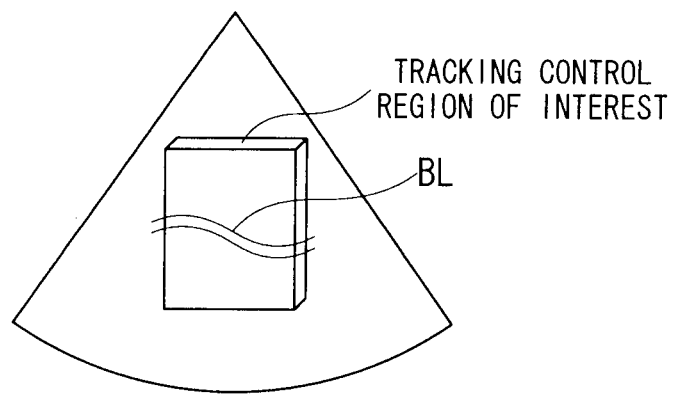
FIGS. 5A and 5B are explanatory diagrams for describing an input method for data related to a region of interest for a three dimensional tracking control where tracking of a Doppler sample marker is desired.
Figure 5B:
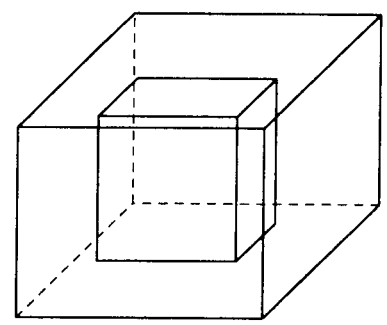

For example, as shown in FIGS. 5A and 5B, the operator inputs data related to a region of interest for a three dimensional tracking control where tracking of the Doppler sample marker of the spectrum Doppler is desired (hereinafter simply referred to as "tracking control region of interest") such that a blood vessel BL is included.

It should be noted that in the case of FIG. 5A, the two dimensional B mode image based on the two dimensional B mode image data and the three dimensional color Doppler image based on the three dimensional color Doppler mode image data displayed on the display unit 14 are simplified images.

It should be noted that while the operator operates the input unit 13, it is possible to input, by as many times as the operator needs, the data related to the three dimensional tracking control region of interest where the tracking of the Doppler sample marker of the spectrum Doppler is desired.

In Step S8, the data obtaining unit 42 determines whether or not data related to a new tracking control region of interest is obtained. That is, after the Doppler sample marker tracking control process is started, in a case where the operator operates the input unit 13 to input the data related to the tracking control region of interest for the first time, it is determined that the data related to the new tracking control region of interest is obtained. In addition, after the operator operates the input unit 13 to input the data related to the tracking control region of interest for the first time, in a case where the operator further operates the input unit 13 to input the data related to the new tracking control region of interest as well, it is determined that the data related to the new tracking control region of interest is obtained.

In Step S8, when it is determined that the data related to the new tracking control region of interest is obtained, the data obtaining unit 42 obtains the data related to the tracking control region of interest input in Step S9 when the operator operates the input unit 13, and supplies the thus obtained data related to the tracking control region of interest to the tracking control region of interest setting unit 43.

In Step S10, the tracking control region of interest setting unit 43 obtains the data related to the tracking control region of interest supplied from the data obtaining unit 42, and on the basis of the thus obtained data related to the tracking control region of interest, sets the three dimensional tracking control region of interest where the tracking of the Doppler sample marker of the spectrum Doppler is desired. Then, the tracking control region of interest setting unit 43 supplies tracking control region of interest set data that is data related to the set tracking control region of interest to the image reconstruction unit 47.

As a result, it is possible to set the three dimensional tracking control region of interest where the tracking of the Doppler sample marker is performed for the blood vessel such as the coronary artery of the heart.

Herein, the beat of the heart includes the diastole phase and the systolic phase. In the diastole phase of the heart, as the blood vessel such as the coronary artery in the vicinity of the heart moves slowly, even when the Doppler sample marker tracking control process is not so frequently executed, a large difference between the actual position of the blood vessel desired to be observed by the operator and the position of the Doppler sample marker does not occur. However, in the systolic phase of the heart, as the blood vessel such as the coronary artery in the vicinity of the heart relatively largely moves, if the Doppler sample marker tracking control process is not frequently executed, the large difference between the actual position of the blood vessel desired to be observed by the operator and the position of the Doppler sample marker occurs.

In view of the above, first, it is determines with use of the detected ECG signal by the ECG signal detection unit 26 whether the current beat of the heart is the diastole phase or the systolic phase. If the current beat of the heart is in the diastole phase, the Doppler sample marker tracking control process for the diastole phase (that is, the Doppler sample marker tracking control process which is not so frequently executed) is executed. On the other hand, if the current beat of the heart is in the systolic phase, the Doppler sample marker tracking control process for the systolic phase (that is, the Doppler sample marker tracking control process which is frequently executed) is executed. Thus, it is possible to execute the Doppler sample marker tracking control process suited to the current beat of the heart. Hereinafter, the Doppler sample marker tracking control process with use of the ECG signal will be described.

In Step S11, the Doppler sample marker tracking control unit 45 obtains the ECG signal supplied form the ECG signal obtaining unit 44.

In Step S12, on the basis of the thus obtained ECG signal, the Doppler sample marker tracking control unit 45 determines whether or not the heart of the subject body is in a diastole phase.

In Step S12, if it is determined that the heart of the subject body is in the diastole phase, in Step S13, the Doppler sample marker tracking control unit 45 executes the Doppler sample marker tracking control process for the diastole phase of the heart. That is, in the diastole phase of the heart, as the blood vessel such as the coronary artery in the vicinity of the heart relatively moves, the Doppler sample marker tracking control process is not so frequently executed. During the diastole phase of one heart beat, for example, the Doppler sample marker tracking control process is executed by three times. It is needless to mention that the present invention is not limited to the above-described case, and a preferred number of times to execute the process during one heart beat may also be set in accordance with the preference of the operator.

On the other hand, in Step S12, if it is determined that the heart of the subject body is in a systolic phase, in Step S14, the Doppler sample marker tracking control unit 45 executes the Doppler sample marker tracking control process for the systolic phase of the heart. That is, in the systolic phase of the heart, as the blood vessel such as the coronary artery in the vicinity of the heart relatively largely moves, the Doppler sample marker tracking control process is frequently executed. During one heart beat in the systolic phase, for example, the Doppler sample marker tracking control process is executed by ten times.

Thus, it is possible to execute the Doppler sample marker tracking control process suited to the current heart beat of the heart. Therefore, the unnecessary Doppler sample marker tracking control process can be suppressed and the efficiency of the control process can be improved.

Figure 4:
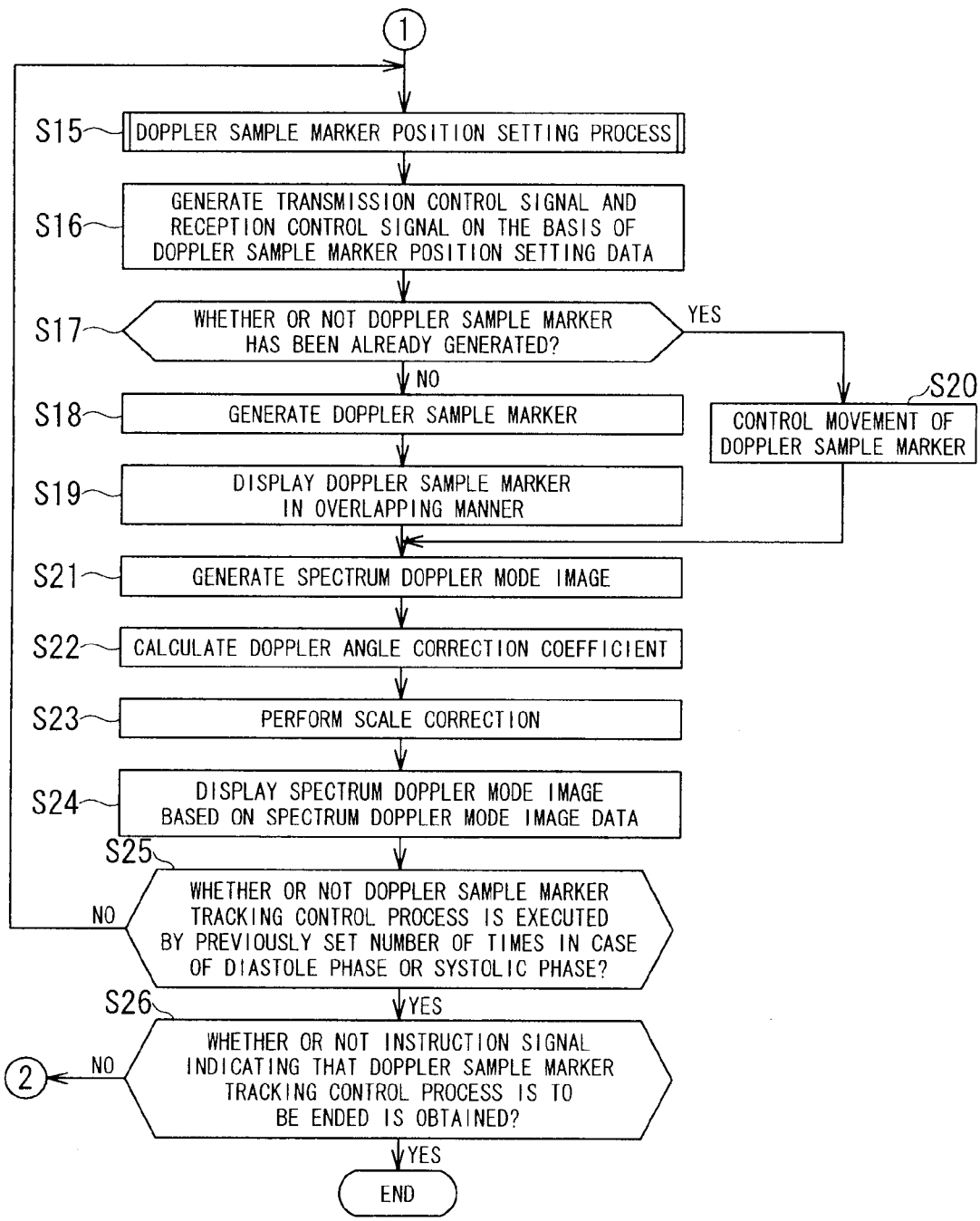
FIG. 4 is a flowchart for describing the Doppler sample marker tracking control process in the ultrasonic diagnostic apparatus of FIG. 2.

In Step S15 of FIG. 4, the ultrasonic diagnostic apparatus 1 executes the Doppler sample marker position setting process. A detail of this Doppler sample marker position setting process is illustrated in a flowchart of FIG. 6.

Figure 6:
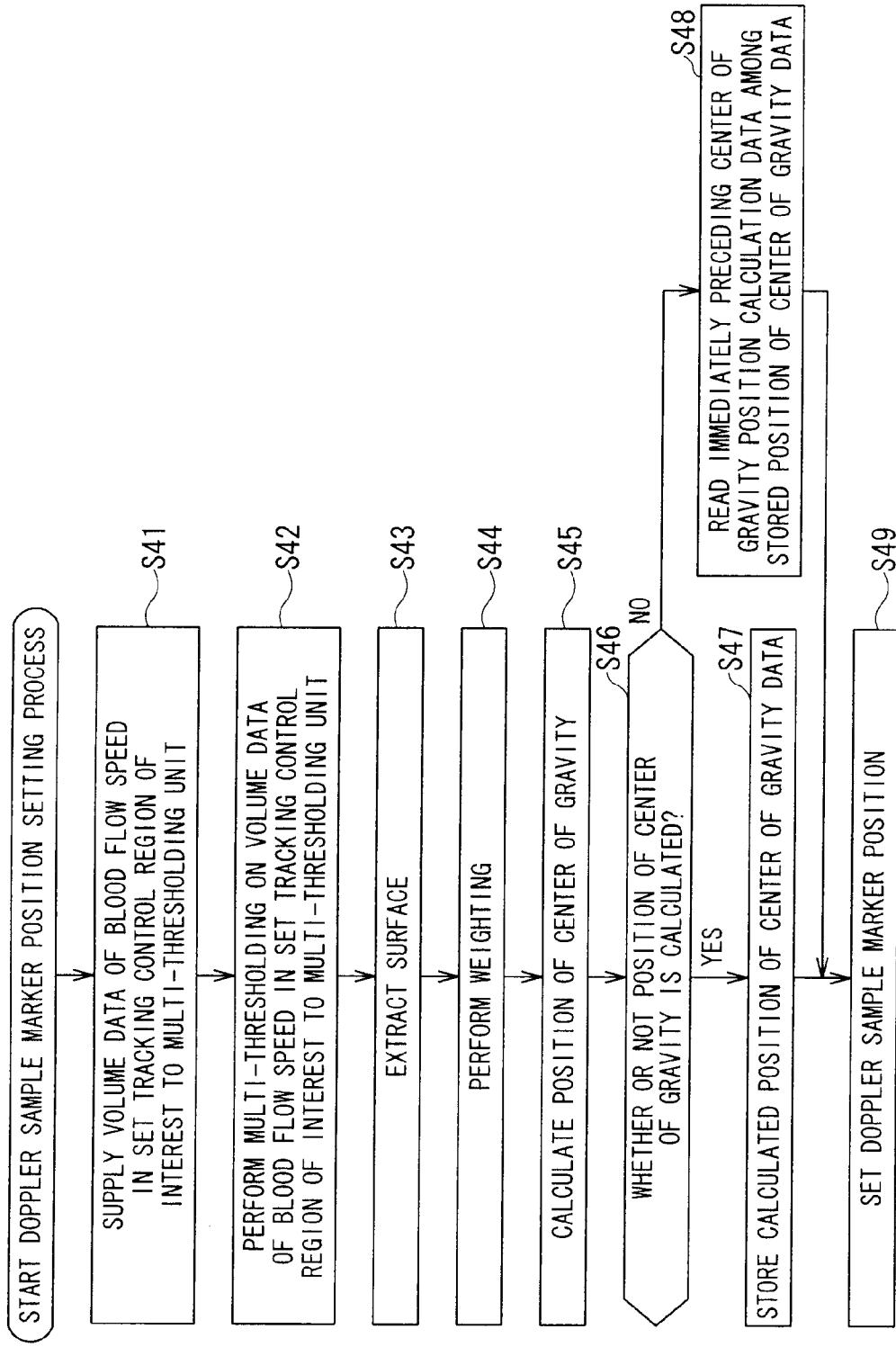
FIG. 6 is a flowchart for describing a detail of a Doppler sample marker position setting process in Step S15 of FIG. 4.

With reference to the flowchart of FIG. 6, the detail of the Doppler sample marker position setting process of the ultrasonic diagnostic apparatus 1 in FIG. 2 will be described.

In Step S41, the image reconstruction unit 47 obtains the tracking control region of interest set data supplied from the tracking control region of interest setting unit 43. Then, in accordance with the control of the Doppler sample marker tracking control unit 45, on the basis of the thus obtained tracking control region of interest set data, the image reconstruction unit 47 reads the volume data of the blood flow speed in the set tracking control region of interest among the volume data of the blood flow speed stored in the main memory unit 41 and supplies the read volume data of the blood flow speed tracking control region of interest to the multi-thresholding unit 48.

In Step S42, the multi-thresholding unit 48 obtains the volume data of the blood flow speed in the tracking control region of interest supplied from the image reconstruction unit 47 and also reads the reference value related to the blood flow speed for performing the multi-thresholding process previously stored in the auxiliary memory unit 49. On the basis of the read reference value related to the blood flow speed, the multi-thresholding unit 48 performs the multi-thresholding process on the thus obtained volume data of the blood flow speed in the tracking control region of interest.

For example, when one reference value A1 is previously stored in the auxiliary memory unit 49 as the reference value related to the blood flow speed for performing the multi-thresholding process, the multi-thresholding unit 48 performs the multi-thresholding process on the thus obtained volume data of the blood flow speed in the tracking control region of interest on the basis of the read reference value A1 related to the blood flow speed.

To be more specific, first, it is sequentially determined whether or not the thus obtained volume data of the blood flow speed is larger than the reference value A1. Next, among the volume data of the blood flow speed, a part determined as smaller than the reference value A1 is set as "0" and a part determined as larger than the reference value A1 is set as "1".

Figure 7:
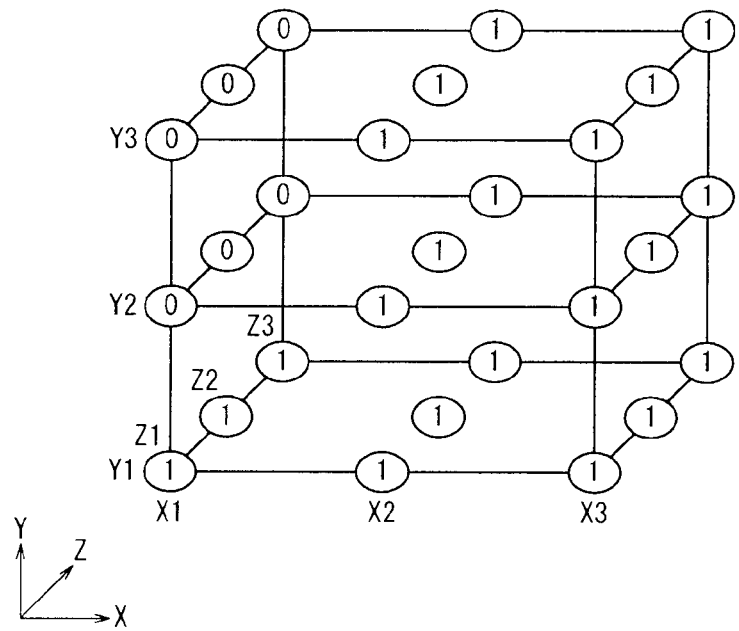
FIG. 7 is an explanatory diagram for describing a multi-thresholding method in a multi-thresholding unit of FIG. 2.

When the volume data related to the blood flow speed is composed of, for example, 27 minute parts, as shown in FIG. 7, if parts located at coordinates (X1, Y2, Z1), coordinates (X1, Y3, Z1), coordinates (X1, Y2, Z2), coordinates (X1, Y3, Z2), coordinates (X1, Y2, Z3), and coordinates (X1, Y3, Z3) are determined as smaller than the reference value A1, the six parts located at the coordinates (X1, Y2, Z1) to the coordinates (X1, Y3, Z3) are set as "0" and the other 21 parts are set as "1".

In addition, when three reference value A1, A2, and A3 (the reference value A1<the reference value A2<the reference value A3) are previously stored in the auxiliary memory unit 49 as the reference values related to the blood flow speed for performing the multi-thresholding process, the multi-thresholding unit 48 quarterizes the thus obtained volume data of the blood flow speed in the tracking control region of interest on the basis of the read reference value A1 to A3 related to the blood flow speed.

To be more specific, first, it is sequentially determined whether or not the thus obtained volume data of the blood flow speed is larger than the reference value A1. Among the volume data of the blood flow speed, a part determined as smaller than the reference value A1 is set as "00". Next, it is determined whether or not the thus obtained volume data of the blood flow speed is larger than the reference value A2. Among the volume data of the blood flow speed, a part determined as larger than the reference value A1 but smaller than the reference value A2 is set as "01".

Furthermore, it is determined whether or not the thus obtained volume data of the blood flow speed is larger than the reference value A3. Among the volume data of the blood flow speed, a part determined as larger than the reference value A2 but smaller the reference value A3 is set as "10" and a part determined as larger than the reference value A3 is set as "11".

Figure 8:
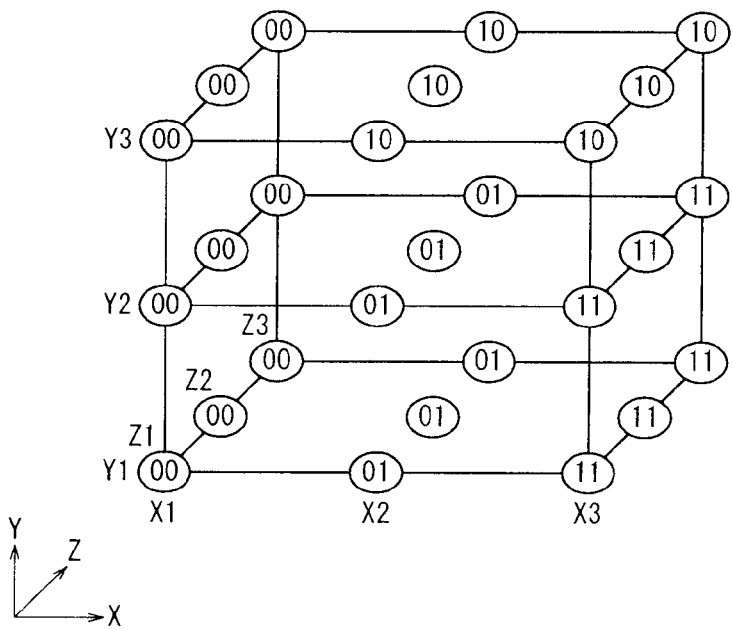
FIG. 8 is an explanatory diagram for describing the multi-thresholding method in the multi-thresholding unit of FIG. 2.

When the volume data related to the blood flow speed is composed of, for example, 27 minute parts, as shown in FIG. 8 for example, 27 parts located at coordinates (X1, Y1, Z1) to coordinates (X3, Y3, Z3) are set as one of "00" to "11".

It is needless to mention that reference values other than one or three (for example, seven reference values, etc.) may be previously stored in the auxiliary memory unit 49 to perform a multi-thresholding process.

According to the embodiment of the present invention, with use of the reference values A1 to A3 previously stored in the auxiliary memory unit 49, the volume data of the blood flow speed in the thus obtained tracking control region of interest is subjected to the multi-thresholding process.

The multi-thresholding unit 48 supplies the multi-threshold volume data that is volume data of the blood flow speed after the multi-thresholding process to the surface extraction unit 50 and the weighting unit 51.

In Step S43, the surface extraction unit 50 obtains the multi-threshold volume data supplied from the multi-thresholding unit 48, and extracts the surface of the blood flow on the basis of the thus obtained multi-threshold volume data.

Here, a concept of an extraction method of extracting the surface of the blood flow on the basis of the multi-threshold volume data will be described.

In general, there is a movement (flow) of the blood flow in a part of the blood flow of the subject body, the blood flow speed included in the volume data before the multi-thresholding process is relatively large, but in a part that is not the blood flow (for example, the blood flow wall, the cardiac wall, etc.), the movement is not so obvious as compared with the blood flow part, and the blood flow speed is not so large.

Figure 9:
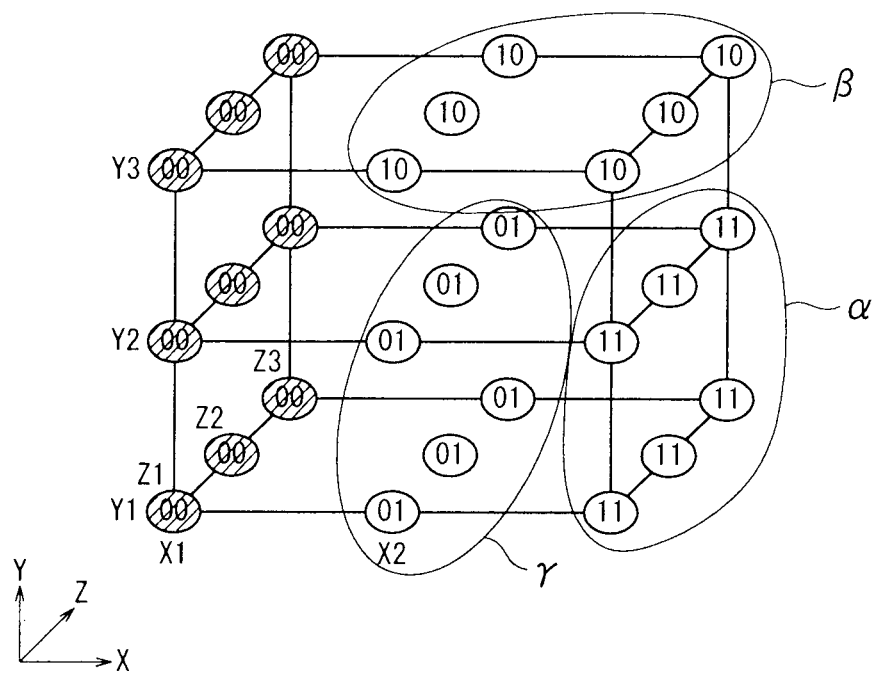
FIG. 9 is an explanatory diagram for describing a surface extraction method in a surface extraction unit of FIG. 2.

In view of the above, a region continuously having parts determined as smaller than the reference value A1 which is the smallest among the three reference values A1 to A3 (parts set as "00" in the multi-thresholding process) when the multi-thresholding process for the volume data of the blood flow speed is performed is defined as a surface of parts which are not the blood flow (hereinafter referred to as "non-blood flow surface"). In the case of the example of FIG. 8, as shown in FIG. 9, the region on the left side can be defined as the non-blood flow surface. Thus, on the basis of the multi-threshold volume data, the non-blood flow surface can be extracted.

Figure 10:
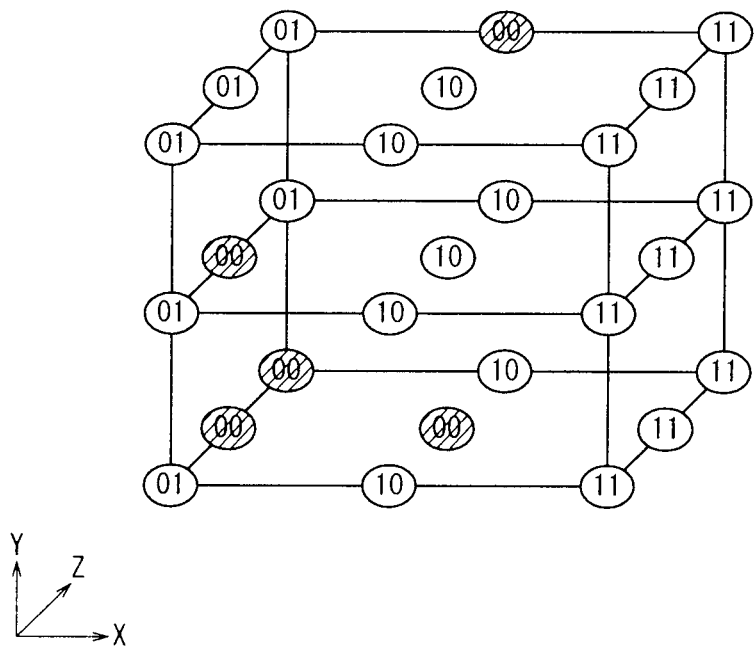
FIG. 10 is an explanatory diagram for describing the surface extraction method in the surface extraction unit of FIG. 2.

It should be noted that when the region continuously having the parts set as "00" in the multi-thresholding process is defined as the non-blood flow surface, for example, as shown in FIG. 9, a region where at least, for example, nine parts set as "00" are continuously present is defined as the non-blood flow surface. Thus, as shown in FIG. 10, a region where specifically the "00" parts are present (a region called black out) when the multi-thresholding process for the volume data of the blood flow speed can be prevented from being extracted as the non-blood flow surface. It is needless to mention that the number of continuous areas set as "00" may be appropriately increased or decreased.

Figure 11:
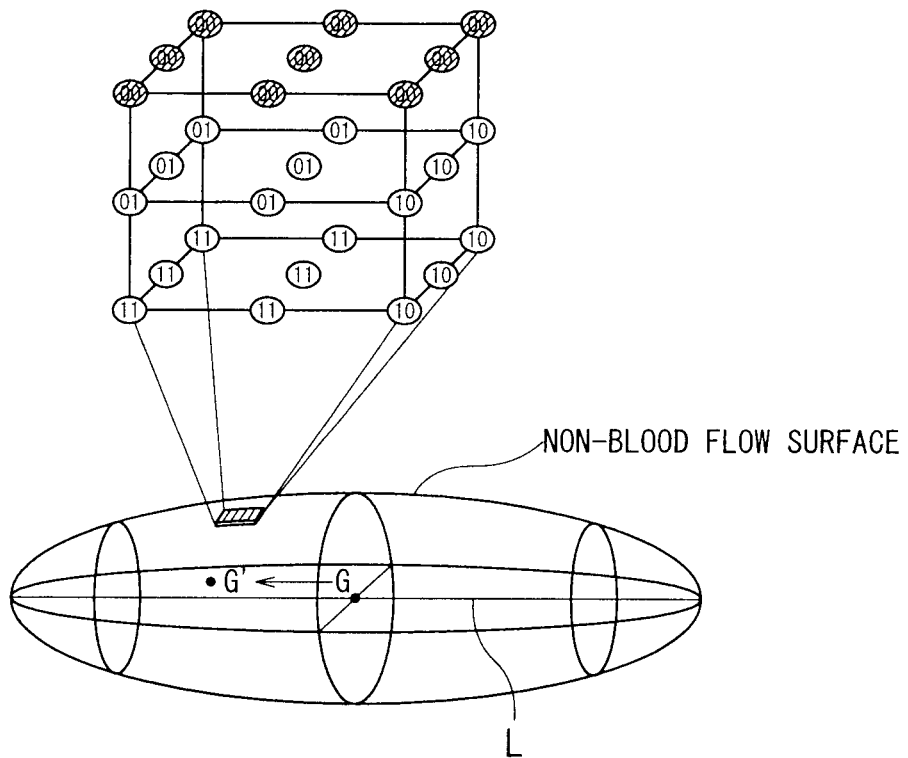
FIG. 11 illustrates an example of a blood flow region extracted in a surface extraction process in Step S43 of FIG. 6.

When such a non-blood flow surface extraction process is repeatedly performed, for example, a space formed by the non-blood flow surfaces shown in FIG. 11 can be extracted. An inner section of this space is an assembly of parts other than "00" set in the multi-thresholding process for the volume data of the blood flow speed (parts set as "01", "10", or "11"). When a consideration is given of a physical continuity of the blood flow, the inner section of this space is thought to be the blood flow region formed by the surfaces of the blood flow.

Therefore, on the basis of the multi-threshold volume data, the surfaces of the blood flow are indirectly extracted by continuously extracting the blood flow surface, it is possible to extract the blood flow region formed by the extracted surfaces of the blood flow.

The surface extraction unit 50 supplies blood flow surface extraction data that is data related to the extracted blood flow surface to the center of gravity position calculation unit 52.

It should be noted that in general the blood vessel is tubular. When the surface extraction process is executed with use of the volume data of the blood flow speed, it is also considerable that the tubular blood flow region is extracted, but in the coronary artery in the vicinity of the heart due to various causes, the closed blood flow region shown in FIG. 11 is expected to be extracted. In view of the above, according to the embodiment of the present invention, for simplicity of the description, a case where the closed blood flow region shown in FIG. 11 is extracted will be described. It is needless to mention that the present invention can be applied not only to the case of the closed blood flow region but also a case where the tubular blood flow region, which is not closed, is extracted.

In Step S44, the weighting unit 51 obtains the multi-threshold volume data supplied from the multi-thresholding unit 48. On the basis of the thus obtained multi-threshold volume data, the weighting unit 51 performs a weighting used when the position of the center of gravity for the blood flow region formed by the blood flow surface (fluid region) is calculated in the center of gravity position calculation unit 52.

For example, in the case of FIG. 9, as a result of performing the multi-thresholding process, it is determined that respective parts in a region α are larger than the reference value A3 related to the blood flow speed and are set as "11". This state represents that the blood flow speed in the region α in the three dimensional space formed by the 27 minute parts is the high speed.

Then, it is determined that respective parts in a region β are larger than the reference value A2 related to the blood flow speed but smaller than A3 and are set as "10". This state represents that the blood flow speed in the region β in the three dimensional space formed by the 27 minute parts is the middle speed.

Furthermore, it is determined that respective parts in a region γ are larger than the reference value the reference value A1 related to the blood flow speed but smaller than A2 and are set as "01". This state represents that the blood flow speed in the region γ in the three dimensional space formed by the 27 minute parts is the low speed.

Therefore, with use of the multi-threshold volume data, in the blood flow region formed by the blood flow surface (for example, the blood flow region of FIG. 11), the high speed region, the middle speed region, and the low speed region of the blood flow can be determined.

It should be noted that if more reference values are used in the multi-thresholding process in Step S42, the speed region with a higher precision can be determined in the blood flow region formed by the blood flow surface.

Moreover, the high speed region, the middle speed region, and the low speed region of the blood flow determined with use of the multi-threshold volume data are respectively provided with, for example, "3", "2", and "1" as weighting coefficients used when the position of the center of gravity of the blood flow region formed by the blood flow surface is calculated in the center of gravity position calculation unit 52.

As a result, when the position of the center of gravity of the blood flow region formed by the blood flow surface is calculated in the center of gravity position calculation unit 52, the high speed region of the blood flow can be calculated to the position of the center of gravity of the blood flow region. It is needless to mention that in order to calculate the middle speed region of the blood flow to the position of the center of gravity of the blood flow region, the high speed region, the middle speed region, and the low speed region of the blood flow may be respectively provided with, for example, "2", "3", and "1" as the weighting coefficients. Also, in accordance with the preference of the operator, while the operator operates the input unit 13, the predetermined weighting coefficients may be changed.

It should be noted that according to the embodiment of the present invention, a description will be given of a case where the operator previously performs such a setting that the high speed region of the blood flow is calculated to the position of the center of gravity of the blood flow region.

The weighting unit 51 supplies the weighting result to the center of gravity position calculation unit 52.

In Step S45, the center of gravity position calculation unit 52 obtains the blood flow surface extraction data supplied from the surface extraction unit 50 and also obtains the weighting result supplied from the weighting unit 51. On the basis of the multi-threshold volume data and the weighting result thus obtained, the center of gravity position calculation unit 52 calculates the position of the center of gravity of the blood flow region formed by the blood flow surface.

In the case of the example of FIG. 11, if the weighting process in Step S44 is not performed, coordinates of a position G as the position of the center of gravity of the blood flow region are calculated. If the weighting process is performed, coordinates of a position G', for example, as the position of the center of gravity of the blood flow region are calculated.

In Step S46, the center of gravity position calculation unit 52 determines whether or not the position of the center of gravity is calculated. That is, when the blood flow region is not extracted in the surface extraction process in Step S43 and accordingly the position of the center of gravity is not calculated, it is determined in Step S46 that the position of the center of gravity is not calculated. On the other hand, when the blood flow region is extracted in the surface extraction process in Step S43 and accordingly the position of the center of gravity can be calculated, it is determined in Step S46 that the position of the center of gravity is calculated.

In Step S46, when it is determined that the position of the center of gravity is calculated, the center of gravity position calculation unit 52 supplies center of gravity calculation data, which is the calculation result, to the main memory unit 41 and the Doppler sample marker position setting unit 53.

In Step S47, the main memory unit 41 obtains the center of gravity position calculation data supplied from the center of gravity position calculation unit 52 and stores the thus obtained center of gravity position calculation data.

In Step S46, when it is determined that the position of the center of gravity is not calculated (that is, the blood flow region is not extracted in the surface extraction process and the position of the center of gravity cannot be calculated), in Step S48, the center of gravity position calculation unit 52 reads the immediately preceding center of gravity position calculation data among the center of gravity position calculation data stored in the main memory unit 41 and supplies the immediately preceding center of gravity position calculation data thus read to the Doppler sample marker position setting unit 53.

It should be noted that it is determined that the position of the center of gravity is not calculated in the Doppler sample marker tracking control process performed for the first time, the immediately preceding center of gravity position calculation data is not stored in the main memory unit 41, and thus cannot be read from the main memory unit 41. In view of the above, in such a case, the last position data related to the Doppler sample marker position manually input by the operator is supplied to the Doppler sample marker position setting unit 53. Thus, it is possible to set the Doppler sample marker to the last Doppler sample marker position manually input.

In Step S49, the Doppler sample marker position setting unit 53 obtains the center of gravity position calculation data supplied from the center of gravity position calculation unit 52. On the basis of the thus obtained center of gravity position calculation data, the Doppler sample marker position setting unit 53 sets the position of the center of gravity for the calculated blood flow region to the position of the Doppler sample marker and supplies the Doppler sample marker position setting data, which is the data related to the set position of the Doppler sample marker, to the spectrum Doppler mode process unit 34, the Doppler sample marker generation unit 54, the Doppler sample marker movement control unit 55, and the transmission and reception control unit 56.

According to the embodiment of the present invention, on the basis of the volume data (for example, the volume data of the blood flow speed), the blood flow region formed by the blood flow surface is extracted, the desired position of the center of gravity for the extracted blood flow region is calculated, and the Doppler sample marker position is set to the calculated desired position of the center of gravity for the blood flow region, whereby it is possible to set the Doppler sample marker to the desired position in the blood vessel.

It should be noted that extraction of a plurality of blood flow regions in the surface extraction process in Step S43 is also conceivable. In such a case, among the extracted blood flow regions, it may be previously set that the blood flow region with a larger volume is used to perform the Doppler sample marker position setting process or in accordance with the preference of the operator, one of the blood flow regions may be used to perform the Doppler sample marker position setting process.

Also, when the plurality of blood flow regions are extracted, the shape of the extracted blood flow region (for example, an S shape, a tube shape, etc.) is stored through the already executed Doppler sample marker tracking control process, a cross-correlation factor (degree of similarity) between the shape of the stored blood flow region and the shape of the newly extracted blood flow region is calculated. With use of the calculated cross-correlation factor, it is determined whether or not the blood flow regions are substantially the identical regions to each other, and only when it is determined that the blood flow regions are substantially the identical regions to each other, a movement control process for the Doppler sample marker as will be described later may be performed.

With reference to FIG. 4 again, in Step S16, the transmission and reception control unit 56 obtains the Doppler sample marker position setting data supplied from the Doppler sample marker position setting unit 53. When the spectrum Doppler mode image data is generated on the basis of the thus obtained Doppler sample marker position setting data, the transmission and reception control unit 56 generates a transmission control signal and a reception control signal for transmitting and receiving the ultrasonic wave on a scanning line including the set position of the Doppler sample marker and supplies the transmission control signal and the reception control signal thus generated to the transmission unit 22 and the reception unit 23, respectively.

It should be noted that the transmission and reception control unit 56 supplies ultrasonic beam direction data that is data related to an ultrasonic beam direction in which the ultrasonic waves are transmitted and received on the scanning line including the set position of the Doppler sample marker to the Doppler angle correction factor calculation unit 57.

In Step S17, the Doppler sample marker generation unit 54 determines whether or not the Doppler sample marker has been already generated (that is, determines whether or not the first Doppler sample marker tracking control process is executed).

In Step S17, when it is determined that the Doppler sample marker is not generated yet, the Doppler sample marker generation unit 54 obtains in Step S18 the Doppler sample marker position setting data supplied from the Doppler sample marker position setting unit 53. On the basis of the thus obtained Doppler sample marker position setting data, the Doppler sample marker generation unit 54 generates the Doppler sample marker already having the set predetermined width with the position of the Doppler sample marker as the center, and supplies to Doppler sample marker generation data that is data related to the thus generated Doppler sample marker to the display unit 14.

Figure 12A:
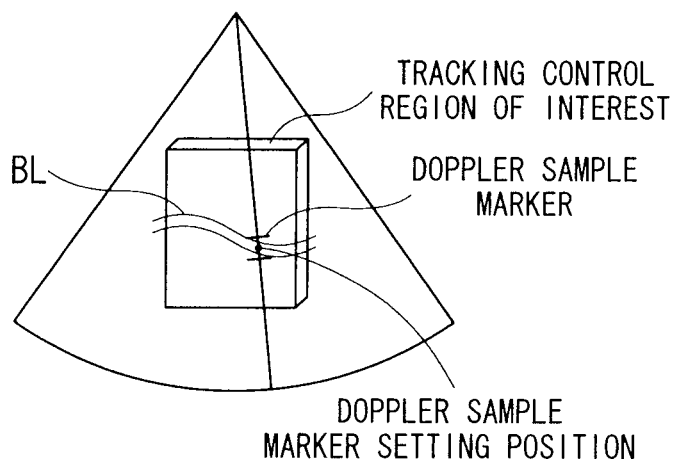
FIG. 12 illustrates a display example of a Doppler sample marker displayed on a display unit of FIG. 1.
Figure 12B:
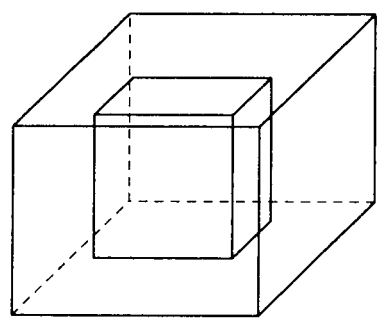

In Step S19, the display unit 14 obtains the Doppler sample marker generation data supplied from the Doppler sample marker generation unit 54. On the basis of the thus obtained Doppler sample marker generation data, the display unit 14 displays the Doppler sample marker at the set predetermined position as shown in FIGS. 12A and 12B while being overlapped with the B mode image based on the already displayed two dimensional B mode image data and the three dimensional color Doppler mode image based on the three dimensional color Doppler mode image data.

As a result, it is possible to display the Doppler sample marker at the predetermined position set in the Doppler sample marker position setting process (that is, the position of the center of gravity of the blood flow region). Therefore, it is possible to simply and precisely perform the tracking of the spectrum Doppler sample marker in accordance with the three dimensional movement of the blood vessel.

On the other hand, in Step S17, when it is determined that the Doppler sample marker has been already generated (that is, when the Doppler sample marker tracking control process has been already executed once, and the Doppler sample marker is generated and already displayed on the display unit 14), the Doppler sample marker generation unit 54 does not newly generate the Doppler sample marker, but generates an instruction signal indicating that the Doppler sample marker has been already generated and supplies the instruction signal to the Doppler sample marker movement control unit 55.

In Step S20, on the basis of the instruction signal supplied from the Doppler sample marker generation unit 54, the Doppler sample marker movement control unit 55 recognizes that the Doppler sample marker has been already generated and also obtains the Doppler sample marker position setting data supplied from the Doppler sample marker position setting unit 53. On the basis of the thus obtained Doppler sample marker position setting data, the Doppler sample marker movement control unit 55 generates a Doppler sample marker movement control signal for controlling the movement of the Doppler sample marker already displayed on the display unit 14. The Doppler sample marker movement control unit 55 supplies the thus generated Doppler sample marker movement control signal to the display unit 14.

As shown in FIGS. 13A and 13B, the display unit 14 moves and displays the already displayed Doppler sample marker on the basis of the Doppler sample marker movement control signal supplied from the Doppler sample marker movement control unit 55.

As a result, it is possible to move the Doppler sample marker to the position of the Doppler sample marker, which is newly set in the Doppler sample marker position setting process. Therefore, it is possible to simply and precisely perform the tracking of the spectrum Doppler sample marker in accordance with the three dimensional movement of the blood vessel.

In Step S21, the spectrum Doppler mode process unit 34 generates the spectrum Doppler image data. That is, the following process will be performed.

The transmission unit 22 transmits an ultrasonic beam for generating the spectrum Doppler mode image data to the subject body on the basis of the transmission control signal supplied from the transmission and reception control unit 56. That is, ultrasonic waves are transmitted and received on the scanning line including the set position of the Doppler sample marker.

To be more specific, on the basis of the transmission control signal supplied from the transmission and reception control unit 56, the rate pulsar of the transmission unit 22 generates a rate pulse for setting a pulse repetition frequency of the ultrasonic pulse entering the inside of the subject body as a predetermined pulse repetition frequency and supplies the rate pulse to the transmission delay circuit. Also, on the basis of the transmission control signal supplied from the transmission and reception control unit 56, the transmission delay circuit adds a delay time to the rate pulse supplied from the rate pulse generator so that the focal position and the deflection angle of the ultrasonic beam at the time of the transmission become a predetermined focal position and a predetermined deflection angle ($\theta\alpha$), before being supplied to the pulsar. Furthermore, the pulsar generates a high pressure pulse for driving the ultrasonic wave transducer on the basis of the rate pulse supplied from the transmission delay circuit and outputs the thus generated high pressure pulse to the ultrasonic probe 12. The ultrasonic probe 12 converts the high pressure pulse that is input from the transmission unit 22 into a high pressure pulse (electric pulse) and transmits the converted ultrasonic pulse to the subject body. A part of the ultrasonic wave transmitted to the inside of the subject body is reflected by a boundary surface between organs inside the subject body or tissues and blood flows having different acoustic impedances.

The ultrasonic probe 12 converts the reflected wave reflected by the subject body into an electric signal and outputs the electric signal to the main body 11. On the basis of the reception control signal supplied from the transmission and reception control unit 56, the reception unit 23 amplifies the reception signal input from the ultrasonic probe 12, adds a predetermined time, and supplies the signal to the spectrum Doppler mode process unit 34 of the image data generation unit 24. That is, the preamplifier of the reception unit 23 obtains a reception signal based on a reflection pulse of an ultrasonic pulse entering the subject body from the ultrasonic probe 12, amplifies the thus obtained reception signal to a predetermined level, and supplies the amplified reception signal to the A/D converter. The A/D converter converts the reception signal supplied from the preamplifier from an analog signal to a digital signal and supplies the signal to the reception delay circuit.

The reception delay circuit gives, on the basis of the reception control signal supplied from the transmission and reception control unit 56, a delay time (a delay time corresponding to a difference in ultrasonic wave propagation times from the focal positions of the respective ultrasonic wave transducers) necessary for determining a reception directivity to the reception signal after the A/D conversion that has been supplied from the A/D converter, and the signal is supplied to the adder. The adder adds the reception signals from the respective ultrasonic wave transducers which are supplied from the reception delay circuit and supplies the added reception signal to the spectrum Doppler mode process unit 34.

After that, in order to generate the spectrum Doppler image data, the transmission and reception of the ultrasonic waves are repeated by a predetermined times on the same scanning line including the set position of the Doppler sample marker.

The Doppler shift signal detector of the spectrum Doppler mode process unit 34 mainly performs an orthogonal phase detection or the like on the reception signal supplied from the reception unit 23 and supplies the detected Doppler shift signal to the analysis unit.

The FFT analyzer of the spectrum Doppler mode process unit 34 obtains the Doppler sample marker position setting data supplied from the Doppler sample marker position setting unit 53. On the basis of the thus obtained Doppler sample marker position setting data, at a predetermined width with the position of the Doppler sample marker as the center, the FFT analyzer performs the FFT analysis on the Doppler shift signal supplied from the Doppler shift signal detector. The computation section performs a computation such as a center frequency, dispersion, or the like, with respect to the frequency spectrum from the FFT analyzer and supplies the spectrum Doppler mode image data generated from the computation to the main memory unit 41.

As a result, it is possible to generate the spectrum Doppler mode image data at the predetermined width with the set Doppler sample marker position as the center in the Doppler sample marker position setting process. Therefore, the spectrum Doppler mode image data of the blood vessel desired to be observed by the operator can be generated, and as a result it is possible to improve the reliability and the stability in the coronary artery diagnosis of the heart with use of the ultrasonic diagnostic apparatus 1.

The main memory unit 41 obtains the spectrum Doppler image data supplied from the spectrum Doppler mode process unit 34 and stores the thus obtained spectrum Doppler image data.

Incidentally, the blood flow speed detected in the spectrum Doppler mode process unit 34 is the blood flow speed with only the component in the ultrasonic beam direction among the Doppler shift actually received from the blood flow of the subject body. For that reason, in order to display the accurate blood flow speed, it is necessary that an angle defined by the flowing direction of the blood flow and the ultrasonic beam direction is calculated, and the detected blood flow speed is corrected with use of the calculated angle such that the accurate blood flow speed is obtained. Hereinafter a description will be given of a Doppler angle correction process.

In Step S22, the Doppler angle correction factor calculation unit 57 obtains the blood flow surface extraction data supplied from the surface extraction unit 50 and also obtains the ultrasonic beam direction data supplied from the transmission and reception control unit 56. On the basis of the blood flow surface extraction data and the ultrasonic beam direction data thus obtained, the Doppler angle correction factor calculation unit 57 calculates an angle β defined by the longitudinal direction in the blood flow region and the ultrasonic beam direction.

To be more specific, the blood flow has a larger continuity depending on a flowing direction. It can be considered that one of longitudinal directions in the blood flow region formed by the surface of the blood flow is the movement direction of the blood flow. For example, in the case of in the case of FIG. 11, it can be considered that one of the longitudinal directions in the blood flow region is one of directions parallel to a straight line L.

As a result, the longitudinal directions in the blood flow region and the ultrasonic beam direction included in the ultrasonic beam direction data supplied from the transmission and reception control unit 56 are known, and therefore it is possible to calculate the angle β defined by the longitudinal direction in the blood flow region and the ultrasonic beam direction.

Next, in order to obtain the accurate blood flow speed, an angle correction coefficient multiplied to the generated spectrum Doppler mode image data is calculated with use of the calculated angle β. As illustrated in FIG. 14, an angle correction coefficient (1/cos β) for correcting a blood flow speed v detected in the spectrum Doppler mode process unit 34 into an accurate blood flow speed V is calculated. The Doppler angle correction factor calculation unit 57 supplies angle correction factor data that is data related to the calculated angle correction coefficient to the scale correction unit 58.

In Step S23, the scale correction unit 58 reads the spectrum Doppler mode image data stored in the main memory unit 41 and also obtains the angle correction factor data supplied from the Doppler angle correction factor calculation unit 57. The scale correction unit 58 corrects the scale by multiplying the thus read spectrum Doppler mode image data by the angle correction factor and supplies the spectrum Doppler image data after the correction to the spectrum Doppler imaging process unit 27.

It should be noted that the Doppler angle correction process may be performed at all the time, performed for each frame rate of the three dimensional color Doppler mode image data, or performed at predetermined time intervals previously set by the operator. It is needless to mention that the frequency of the Doppler angle correction process may be appropriately changed in accordance with the preference of the operator during the Doppler sample marker tracking control process.

According to the embodiment of the present invention, the actual flowing direction of the blood flow is estimated from the longitudinal direction of the extracted blood flow region and the estimated flowing direction of the blood flow and the beam direction of the ultrasonic wave are used to calculate the angle correction coefficient, whereby it is possible to calculate the actual blood flow speed with a higher precision.

The spectrum Doppler imaging process unit 27 obtains the spectrum Doppler mode image data after the scale correction supplied from the scale correction unit 58. Then, the spectrum Doppler imaging process unit 27 performs the imaging process on the thus obtained spectrum Doppler mode image data after the scale correction to be supplied to the display unit 14 so that the spectrum Doppler mode image data after the scale correction can be displayed as the spectrum of the temporal change in the Doppler shift frequency (the value corresponding to the speed) is displayed on the display unit 14.

In Step S24, the display unit 14 obtains supplied from the spectrum Doppler imaging process unit 27 the spectrum Doppler mode image data after the correction and displays a spectrum Doppler mode image based on the thus obtained spectrum Doppler mode image data after the correction.

As a result, while the operator observes the spectrum Doppler mode image of the blood vessel desired to be observed, the diagnosis can be performed on the blood vessel desired to be observed. Therefore, it is possible to improve the reliability and the stability in the coronary artery diagnosis of the heart with use of the ultrasonic diagnostic apparatus 1.

In Step S25, the Doppler sample marker tracking control unit 45 determines whether or not the Doppler sample marker tracking control process is executed by the previously set number of times in the case of the diastole phase or the systolic phase. That is, at this stage, in a case where the Doppler sample marker tracking control process for the diastole phase is executed, when such a setting is made that the Doppler sample marker tracking control process is executed, for example, by three times, during the diastole phase in one heart beat, it is determined whether or not the Doppler sample marker tracking control process is executed by three times during the diastole phase in one heart beat.

Also, at this stage, in a case where the Doppler sample marker tracking control process for the systolic phase is executed, when such a setting is made that the Doppler sample marker tracking control process is executed, for example, by ten times during the systolic phase in one heart beat, it is determined whether or not the Doppler sample marker tracking control process is executed by ten times during the systolic phase in one heart beat.

In Step S25, when it is determined that the Doppler sample marker tracking control process is not executed by the previously set number of times in the case of the diastole phase or the systolic phase, the Doppler sample marker tracking control unit 45 controls the image reconstruction unit 47 such that the Doppler sample marker tracking control process is to be executed by the remaining number out of the previously set number of times. Then, the process returns to Step S15, and after that, the processes in Step S15 and subsequent steps are repeatedly performed. Thus, the Doppler sample marker tracking control process can be repeatedly performed by the previously set number of times during the diastole phase or the systolic phase in one heart beat.

In Step S25, when it is determined that the Doppler sample marker tracking control process is executed by the previously set number of times in the case of the diastole phase or the systolic phase, the Doppler sample marker tracking control unit 45 determines whether or not the instruction signal indicating that the Doppler sample marker tracking control process is to be ended, which is supplied from the data obtaining unit 42, is obtained in Step S26.

That is, when the operator operates the Doppler sample marker tracking end button (not shown) of the input unit 13, and the data obtaining unit 42 obtains the data related to the instruction indicating that the Doppler sample marker tracking control process is to be ended. On the basis of the data related to the instruction indicating that the Doppler sample marker tracking control process is to be ended, the data obtaining unit 42 generates the instruction signal indicating that the Doppler sample marker tracking control process is to be ended and supplies the signal to the Doppler sample marker tracking control unit 45.

The Doppler sample marker tracking control unit 45 determines whether or not the instruction signal indicating that the Doppler sample marker tracking control process is to be ended, which is supplied from the data obtaining unit 42, is obtained.

Figure 3:
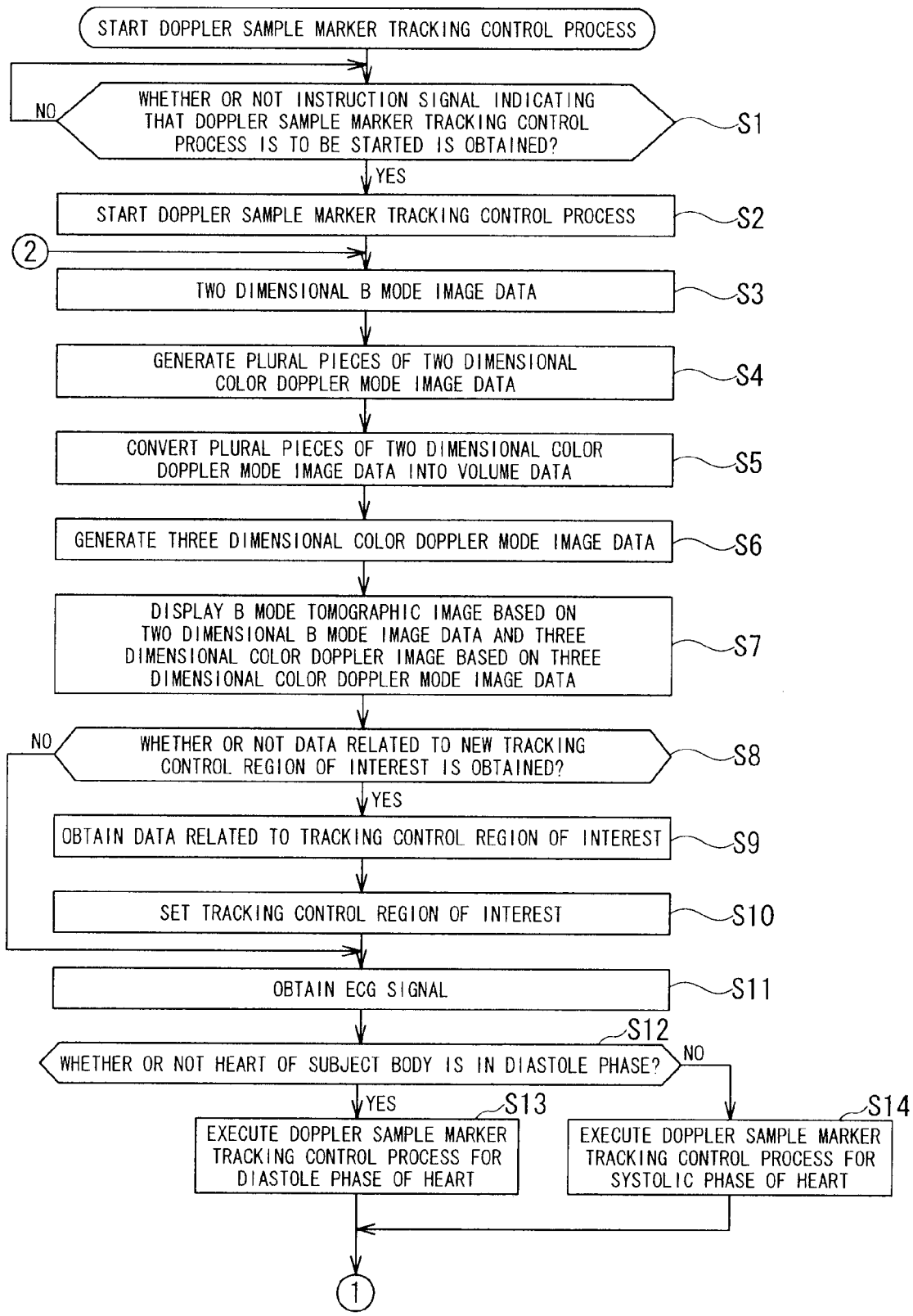
FIG. 3 is a flowchart for describing a Doppler sample marker tracking control process in the ultrasonic diagnostic apparatus of FIG. 2.

In Step S26, when it is determined that the instruction signal indicating that the Doppler sample marker tracking control process is to be ended is not obtained, the process returns to Step S3 of FIG. 3, and after that, the processes in Step S3 and subsequent steps are repeatedly performed in the similar manner.

As a result, at this stage, in a case where the Doppler sample marker tracking control process for the diastole phase is executed, when it is determined as the systolic phase of the heart that on the basis of the thus obtained ECG signal, thereafter, the Doppler sample marker tracking control process for the systolic phase is executed. The similar processes are repeatedly performed after that and, until the operator operates the Doppler sample marker tracking end button (not shown) of the input unit 13 to instruct the end of the Doppler sample marker tracking, the Doppler sample marker tracking control process is repeatedly executed.

Incidentally, according to the embodiment of the present invention, when the Doppler sample marker tracking control process is started, in accordance with the preference of the operator, the desired tracking control region of interest is previously set for the tracking control of the Doppler sample marker. However, as shown in FIGS. 15A and 15B, when a blood vessel BL-1 and a blood vessel BL-2 are present in the tracking control region of interest, for example, if the Doppler sample marker tracking control process is repeatedly executed, the Doppler sample marker position may be moved to both the blood vessel BL-1 and the blood vessel BL-2. When the Doppler sample marker position is frequently moved to a plurality of blood vessels such as the blood vessel BL-1 and the blood vessel BL-2, this is not practical when the operator utilizes for the diagnosis, and also the load of the CPU 29 at the time of the Doppler sample marker tracking control process becomes large. Thus, it takes longer time to perform the Doppler sample marker tracking control process.

In view of the above, while the Doppler sample marker tracking control process is repeatedly executed, when the operator desires the limitation on the movement range of the Doppler sample marker (tracking control range) (that is, when the operator limits the blood vessel desired to be observed), the operator may operate the input unit 13 to input the data related to the new tracking control region of interest in a narrower range so that the tracking control region of interest of the Doppler sample marker is limited.

In this case, it is determined that the data related to the new tracking control region of interest is obtained in Step S8 of FIG. 3, and through the processes in Step S9 and S10, on the basis of the thus obtained data related to the new tracking control region of interest, a new tracking control region of interest is set. After that, in the new tracking control region of interest, the Doppler sample marker tracking control process is repeatedly executed.

As a result, even when the plurality of blood vessels are present in the tracking control region of interest, by newly limiting the tracking control region of interest for the Doppler sample marker, the Doppler sample marker can be only moved in the vicinity of the blood vessel desired to be observed the operator (for example, the blood vessel BL-1, etc., in the case of FIG. 15A).

Therefore, the load on the CPU 29 at the time of the Doppler sample marker tracking control process can be suppressed and the time spent for the Doppler sample marker tracking control process can be reduced. In addition, it is possible to perform the tracking of the Doppler sample marker only for the blood vessel desired to be observed the operator. As a result, it is possible to improve the reliability and the stability in the coronary artery diagnosis of the heart with use of the ultrasonic diagnostic apparatus 1.

It should be noted that as the operator operates the input unit 13 to input the data related to the new tracking control region of interest as many times as desired, the tracking control region of interest where the Doppler sample marker tracking control process is executed can be set in the ultrasonic diagnostic apparatus 1.

Also, the operator operates the input unit 13 to set the new tracking control region of interest in the ultrasonic diagnostic apparatus 1, but the present invention is not limited to in the above-mentioned case. With the use of the moved distance of the blood vessel obtained by repeatedly executing the Doppler sample marker tracking control process, the tracking control region of interest of the Doppler sample marker may be automatically set.

It should be noted that if the data related to the new tracking control region of interest is not input while the operator operates the input unit 13, in Step S8, it is determined that the data related to the new tracking control region of interest is not obtained, and the processes in Steps S9 and S10 are skipped. Then, in the set latest tracking control region of interest, the Doppler sample marker tracking control process is repeatedly executed.

On the other hand, in Step S33, in a case where it is determined that the instruction signal indicating that the Doppler sample marker tracking control process is to be ended, is obtained, the Doppler sample marker tracking control unit 45 ends the Doppler sample marker tracking control process.

It should be noted that according to the embodiment of the present invention, the operator operates a Doppler sample marker tracking control start button or end button (not shown in the drawing) provided to the input unit 13 to start or end the Doppler sample marker tracking control process, but the Doppler sample marker tracking control process may be executed at all the time.

According to the first embodiment of the present invention, the volume data (for example, the volume data of the blood flow speed) is used to extract the blood flow region formed by the blood flow surface. The Doppler sample marker position is set to the desired position of the center of gravity for the extracted blood flow region. The Doppler sample marker is displayed on and moved in the set Doppler sample marker position. At the same time, the set Doppler sample marker position is used to generate the spectrum Doppler mode image data. Thus, the tracking of the spectrum Doppler sample marker can be simply and accurately performed in accordance with the three dimensional movement of the blood vessel desired to be observed. With this configuration, while the operator observes the spectrum Doppler mode image of the blood vessel desired to be observed, the diagnosis of the blood vessel desired to be observed can be performed. Therefore, it is possible to improve the reliability and the stability in the coronary artery diagnosis of the heart with use of the ultrasonic diagnostic apparatus 1.

Figure 17:
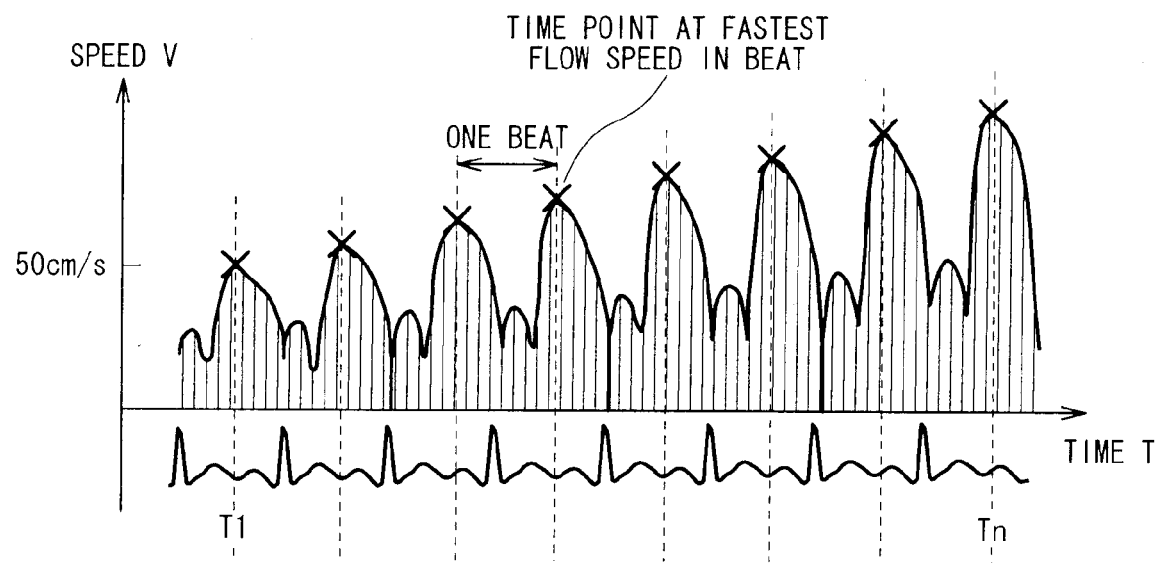
FIG. 17 is an explanatory diagram for describing a movement speed of a coronary artery which changed in accordance with a beat of the heart.

Incidentally, in a case where the coronary arteries in the vicinity of the heart are observed, these coronary arteries move periodically in accordance with the beat of the heart. As shown in FIG. 17, the movement speed of the coronary artery becomes relatively slow in the predetermined time phase in one heart beat (for example, at the time of the breathing of the subject body, etc.), but on the other hand, the movement speed of the coronary artery becomes fastest in another predetermined time phase in one heart beat.

Also, it is clinically significant to observe the time phase in which the movement speed of the coronary artery becomes fastest. In particular, it is strongly desired in the clinic field that the fastest speeds before and after the dosage of medicine can be accurately compared with each other and observed. In view of the above, in order that at least the time phase in which the movement speed of the coronary artery becomes fastest can be observed, the Doppler sample marker tracking control process may be executed only in the time phase in which the movement speed of the coronary artery becomes fastest.

To be more specific, on the basis of the ECG signal supplied form the ECG signal obtaining unit 44, the Doppler sample marker tracking control unit 45 determines whether or not it is the time phase in which the movement speed of the coronary artery becomes fastest. When it is determined that it is the time phase in which the movement speed of the coronary artery becomes fastest, the Doppler sample marker tracking control process may be executed.

It is needless to mention that the frequency is not limited to the one heart beat span. The Doppler sample marker tracking control process may be executed only when the time phase in which the movement speed of the coronary artery becomes fastest for every several beats with an interval. Also, in such a case of synchronizing the heart beat, in accordance with a preference of the operator or a type of the blood vessel, the Doppler sample marker tracking control process may be performed by plural times in one heart beat.

As a result, at least the time phase in which the movement speed of the coronary artery becomes fastest can be observed, and it is possible to improve the process efficiency of the Doppler sample marker tracking control process.

Figure 18A:
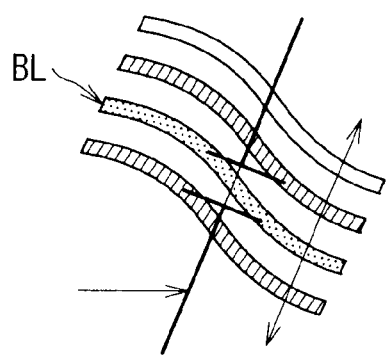
FIG. 18 is an explanatory diagram for describing a setting method for a Doppler sample marker width.
Figure 18B:
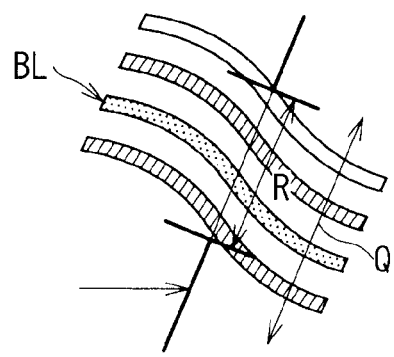

It should be noted that according to the first embodiment of the present invention, as shown in FIG. 18A, the width of the Doppler sample marker is previously generated with the set predetermined width (fixed width), the tracking of the position of the Doppler sample marker having the predetermined width is performed in accordance with the movement of the blood vessel BL (movement in the arrow direction). However, as shown in FIG. 18B, as a result of a statistical computation process regarding a tracking result through the repeatedly executed Doppler sample marker tracking control process, if the movement of the blood vessel BL is only within the range of a width Q, on the basis of the statistical computation process result, the width of the Doppler sample marker (a length of a window function used for a Doppler computation in the spectrum Doppler mode process unit 34) may be changed and at the same time the Doppler sample marker position may be set. Hereinafter, a second embodiment of the present invention which uses this process will be described.

Second Embodiment

Figure 19:
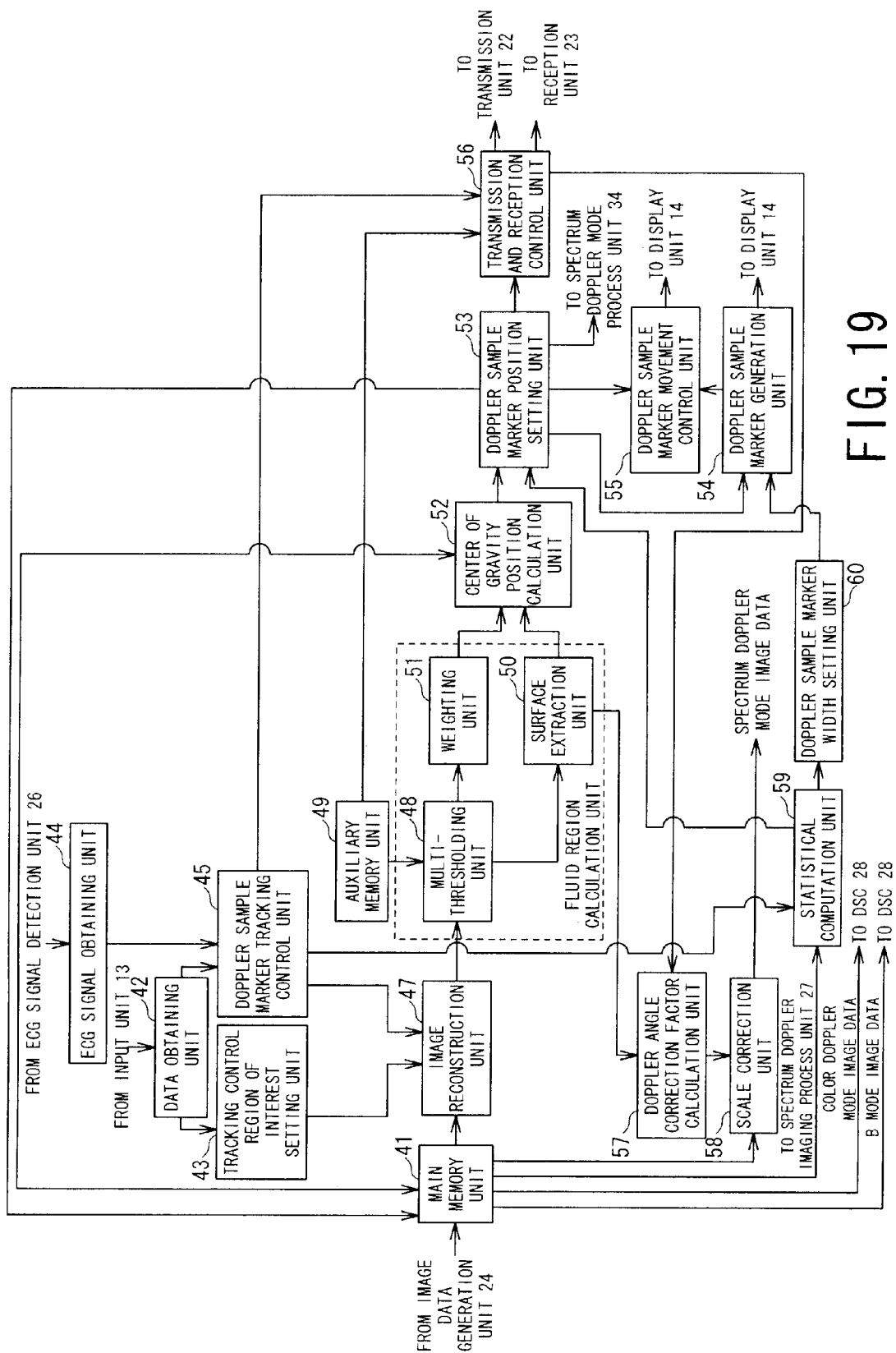
FIG. 19 is a block diagram illustrating a functional configuration executable by the ultrasonic diagnostic apparatus of FIG. 1 according to a second embodiment.

FIG. 19 is a block diagram illustrating a functional configuration executable by the ultrasonic diagnostic apparatus 1 of FIG. 1 according to a second embodiment. It should be noted that the configuration of the ultrasonic diagnostic apparatus 1 of FIG. 1 is similar to the above, and a description thereof will be omitted to avoid the repetition. Also, the same reference numerals are given to the parts corresponding to those in the configuration of the ultrasonic diagnostic apparatus 1 of FIG. 2, and a description thereof will be omitted to avoid the repetition.

A statistical computation unit 59 reads the Doppler sample marker position setting data stored in the main memory unit 41 in accordance with the control of the Doppler sample marker tracking control unit 45, and on the basis of the read Doppler sample marker position setting data, the statistical computation unit 59 performs the statistical computation process.

To be more specific, as the Doppler sample marker tracking control process is executed by 20 times, for example, 20 Doppler sample marker positions are set. When the movement of the Doppler sample marker is limited, the statistical computation unit 59 performs the statistical computation process on the basis of the 20 pieces of the Doppler sample marker position setting data to compute an average position, a standard deviation, and the like of the 20 Doppler sample marker positions.

The statistical computation unit 59 supplies the statistical computation result to the Doppler sample marker position setting unit 53 and a Doppler sample marker width setting unit 60.

The Doppler sample marker width setting unit 60 obtains the statistical computation result supplied from the statistical computation unit 59. On the basis of the thus obtained statistical computation result, the Doppler sample marker width setting unit 60 sets the width of the Doppler sample marker and supplies the Doppler sample marker width setting data that is data related to a width of the set Doppler sample marker to the Doppler sample marker generation unit 54.

Figure 20:
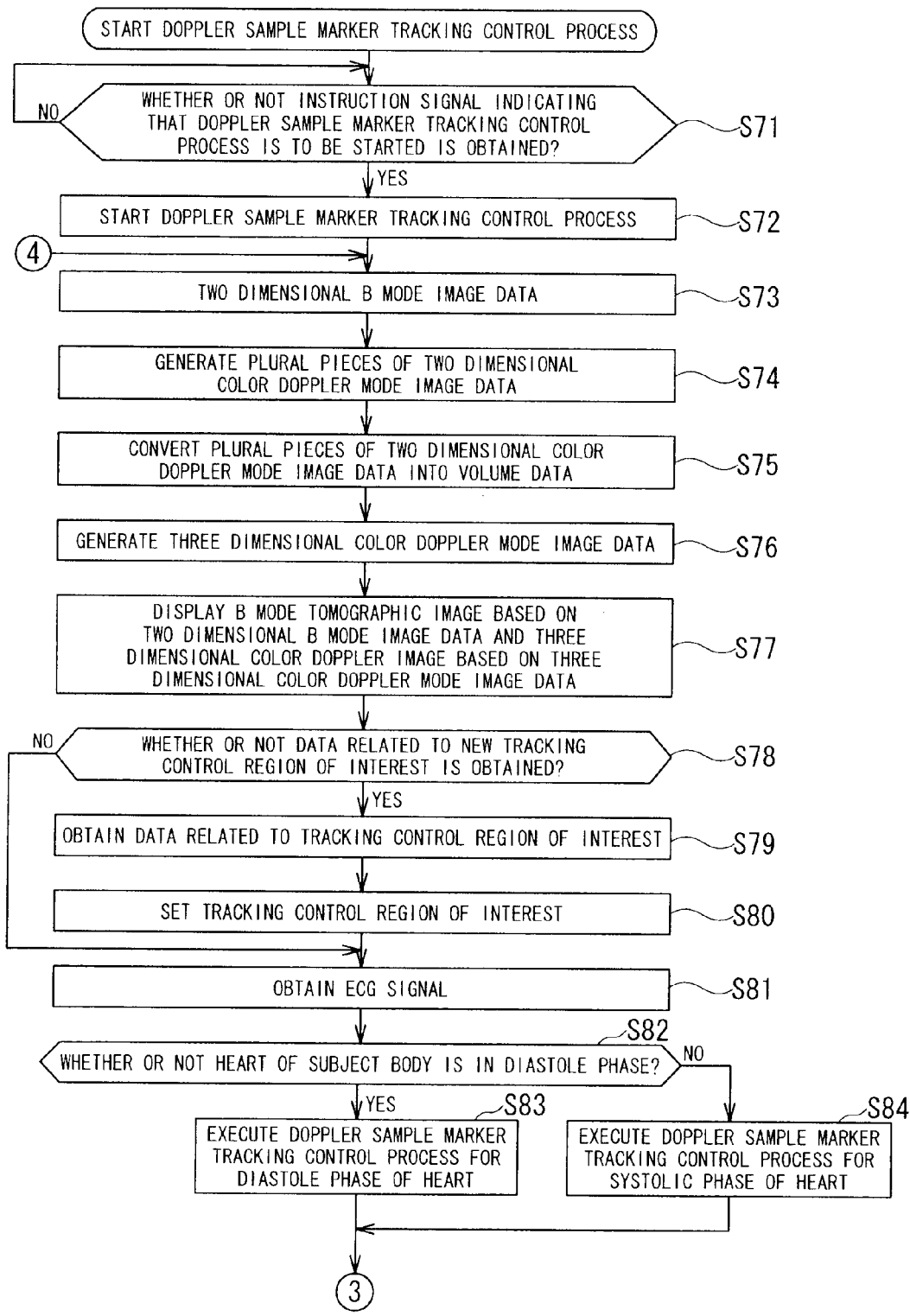
FIG. 20 is a flowchart for describing a Doppler sample marker tracking control process in the ultrasonic diagnostic apparatus of FIG. 19.
Figure 21:
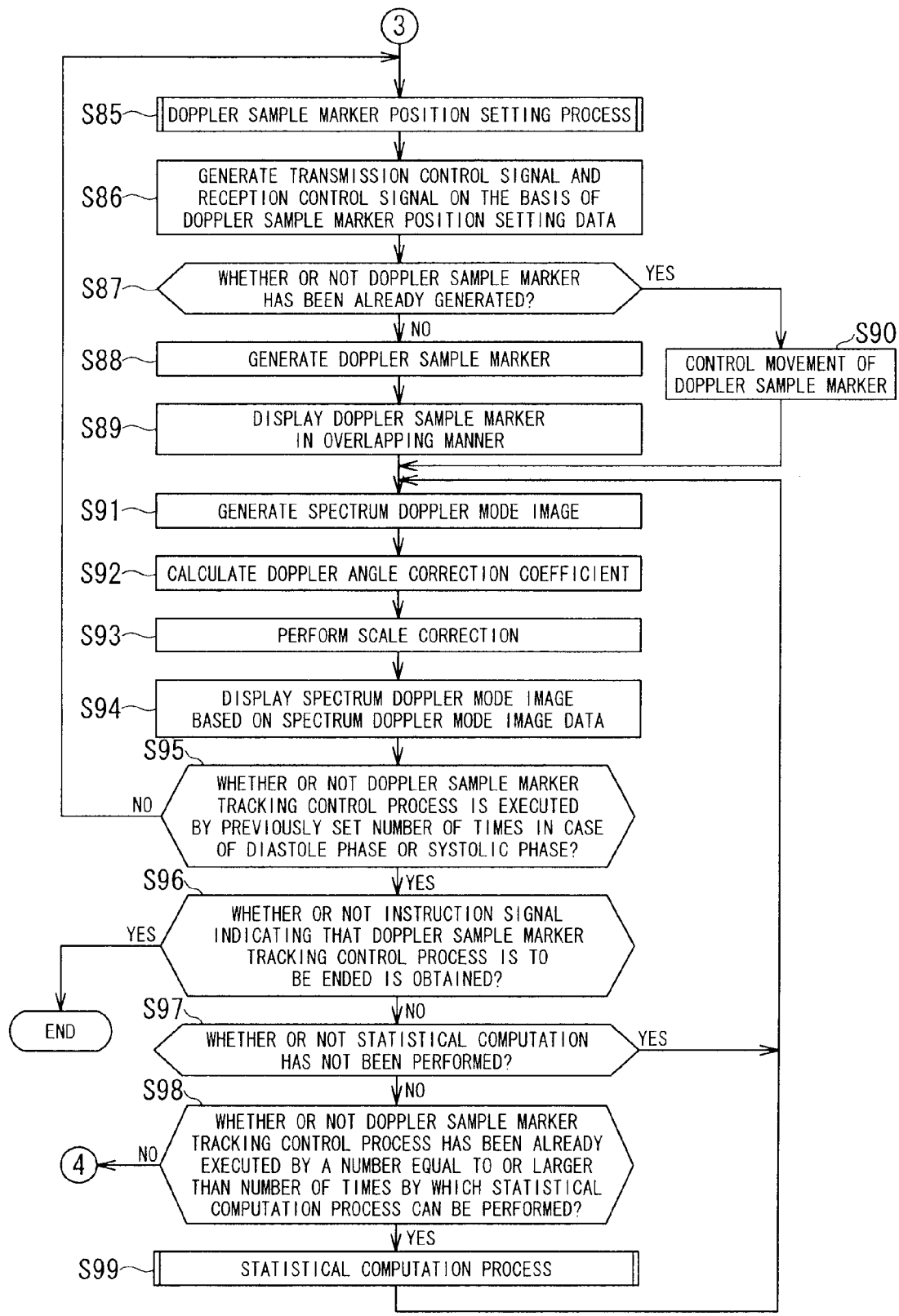
FIG. 21 is a flowchart for describing the Doppler sample marker tracking control process in the ultrasonic diagnostic apparatus of FIG. 19.

Next, with reference to flowcharts of FIGS. 20 and 21, a description will be given of the Doppler sample marker tracking control process of the ultrasonic diagnostic apparatus 1 in FIG. 19. It should be noted that the processes in Steps S71 to S96 of FIGS. 20 and 21 are similar to those in Steps S1 to S26 of FIGS. 3 and 4, and a description thereof will be omitted to avoid the repetition.

In Step S96, when it is determined that the instruction signal indicating that the Doppler sample marker tracking control process is to be ended is not obtained, the Doppler sample marker tracking control unit 45 determines whether or not the statistical computation has been performed in the statistical computation unit 59 in Step S97.

In Step S97, when it is determined that the statistical computation has not been performed in the statistical computation unit 59, the Doppler sample marker tracking control unit 45 determines whether or not the Doppler sample marker tracking control process has been already executed by a number equal to or larger than the number of times by which the statistical computation process can be performed in Step S98.

In Step S98, when it is determined that the Doppler sample marker tracking control process has not been executed yet by the number equal to or larger than the number of times by which the statistical computation process can be performed, the process returns to Step S73, and after that, the processes in Step S73 and subsequent steps are repeatedly performed. Thus, it is possible to execute the Doppler sample marker tracking control process up until the number of times by which the statistical computation process can be performed.

In Step S98, when it is determined that the Doppler sample marker tracking control has been already executed by the number equal to or larger than the number of times by which the statistical computation process can be performed, the Doppler sample marker tracking control unit 45 controls the respective units of the ultrasonic diagnostic apparatus 1 to execute the statistical computation process.

Figure 22:
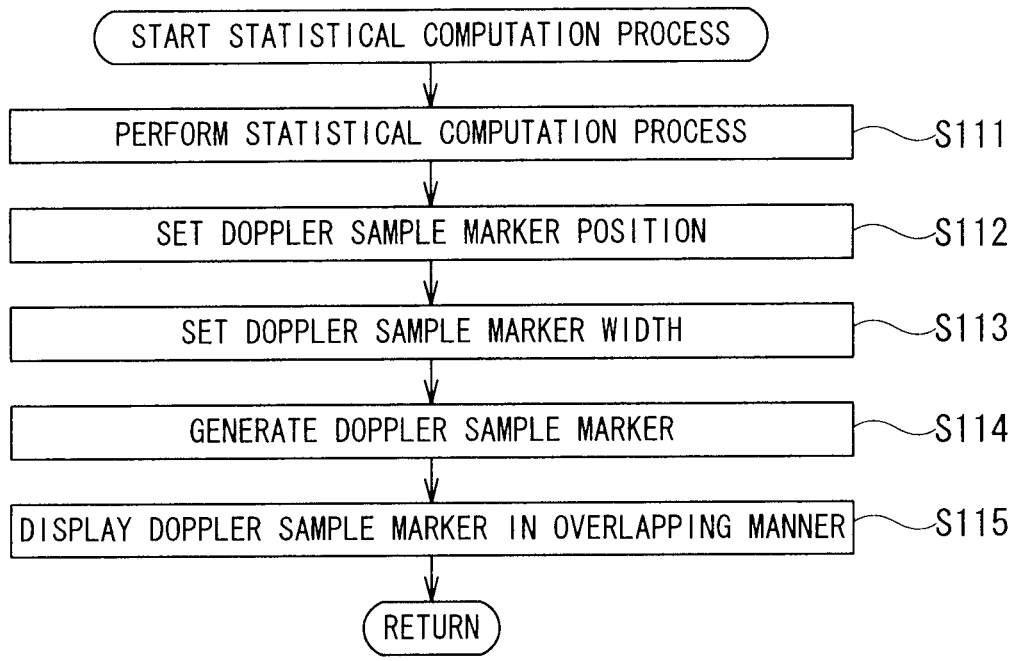
FIG. 22 is a flowchart for describing a detail of a statistical computation process in Step S99 of FIG. 21.

In Step S99, the ultrasonic diagnostic apparatus 1 executes the statistical computation process in accordance with the control of the Doppler sample marker tracking control unit 45. A flowchart of FIG. 22 illustrates a detail of this the statistical computation process.

With reference to a flowchart of FIG. 22, a description will be given of the statistical computation process of the ultrasonic diagnostic apparatus 1 in FIG. 19.

In Step S111, the statistical computation unit 59 reads the plural pieces of the Doppler sample marker position setting data stored in the main memory unit 41 in accordance with the control of the Doppler sample marker tracking control unit 45. On the basis of the plural pieces of the read Doppler sample marker position setting data, the statistical computation unit 59 performs the statistical computation process to calculate an average position (a position which becomes a spatial average), a standard deviation, and the like, of the plural Doppler sample marker positions.

The statistical computation unit 59 supplies data related to the average position data of the plural Doppler sample marker positions as a result of performing the statistical computation process to the Doppler sample marker position setting unit 53. In addition, the statistical computation unit 59 supplies data related to the standard deviation of the plural Doppler sample marker positions to the Doppler sample marker width setting unit 60.

In Step S112, the Doppler sample marker position setting unit 53 obtains the average position data supplied from the statistical computation unit 59. On the basis of the thus obtained average position data, the Doppler sample marker position setting unit 53 sets the Doppler sample marker position to the calculated average position and supplies Doppler sample marker position setting data that is data related to the set Doppler sample marker position to the spectrum Doppler mode process unit 34 and the Doppler sample marker generation unit 54.

In Step S113, the Doppler sample marker width setting unit 60 obtains the standard deviation data supplied from the statistical computation unit 59. On the basis of the thus obtained standard deviation data, the Doppler sample marker width setting unit 60 sets the width of the Doppler sample marker. That is, as shown in FIG. 18B, on the basis of the thus obtained standard deviation data, when it is determined that the blood vessel BL is only moved in the range of the width Q, the width of the Doppler sample marker is set, for example, to a width R.

The Doppler sample marker width setting unit 60 supplies Doppler sample marker width setting data that is data related to the width of the set Doppler sample marker to the Doppler sample marker generation unit 54.

In Step S114, the Doppler sample marker generation unit 54 obtains the Doppler sample marker position setting data supplied from the Doppler sample marker position setting unit 53 and also obtains the Doppler sample marker width setting data supplied from the Doppler sample marker width setting unit 60. On the basis of the thus obtained Doppler sample marker position setting data and the Doppler sample marker width setting data, the Doppler sample marker generation unit 54 generates the new Doppler sample marker and supplies the thus generated new Doppler sample marker generation data via the DSC 28 to the display unit 14.

In Step S115, on the basis of the thus generated new Doppler sample marker generation data, the display unit 14 displays the newly generated Doppler sample marker while being overlapped with the B mode image based on the already displayed two dimensional B mode image data and the three dimensional color Doppler mode image based on the three dimensional color Doppler mode image data.

After that, the process advances to Step S91 of in Step S99, and the processes in Step S91 and subsequent steps are repeatedly performed.

As a result, when the statistical computation process is executed, the position of the displayed Doppler sample marker is fixed to the average position. At the same time, the width of the Doppler sample marker is fixed to the set predetermined width. Also, in the spectrum Doppler mode process unit 34, the FFT analysis or the like is performed on the Doppler shift signal with the average position as the center at the set predetermined width R to generate the spectrum Doppler image data.

On the other hand, in Step S97, when it is determined that the statistical computation has been already performed in the statistical computation unit 59, the process advances to Step S91, and after that, the processes in Step S91 and subsequent steps are repeatedly performed. That is, while keeping the Doppler sample marker position and width fixed after the statistical computation process, the B mode image data, the three dimensional color Doppler mode image data, the spectrum Doppler mode image data, and other data are repeatedly generated and displayed.

According to the second embodiment of the present invention, as the statistical computation process is performed on the basis of the plural pieces of Doppler sample marker position setting data obtained from the repeatedly executed Doppler sample marker tracking control process, it is possible to optimize the position and the width of the Doppler sample marker. With this configuration, the blood vessel desired to be observed the operator can be more easily observed. Therefore, it is possible to improve the reliability and the stability in the coronary artery diagnosis of the heart with use of the ultrasonic diagnostic apparatus 1.

It should be noted that according to the second embodiment of the present invention, the position and the width of the Doppler sample marker is fixed on the basis of the result of the statistical computation process, but the present invention is not limited to the above-mentioned case. The result of the statistical computation process can be used for various processes in the Doppler sample marker tracking control process.

For example, on the basis of the result of the statistical computation process, the Doppler sample marker tracking control process is executed only in the predetermined time phase where the movement of the blood vessel is intense, and the Doppler sample marker tracking control process may not be executed in the predetermined time phase where the movement of the blood vessel is gentle. With this configuration, it is possible to improve the process efficiency of the Doppler sample marker tracking control process.

In addition, the Doppler sample marker position setting process and the like are performed in parallel even after the statistical computation process is executed. After the execution of the first statistical computation process, the statistical computation process is repeatedly executed for every predetermined time. On the basis of the statistical computation result obtained each time, the position or width of the Doppler sample marker may be set. With this configuration, as the Doppler sample marker tracking control process is executed more frequently, the accuracy of the Doppler sample marker tracking control process can be further improved.

Furthermore, on the basis of the result of the statistical computation process in the statistical computation unit 59, the width of the Doppler sample marker is not only set but also, for example, various control information in the ultrasonic diagnostic apparatus 1 such as the transmission and reception conditions suitable at the average position set to the position of the Doppler sample marker (for example, a transmission pulse wavelength, a transmission aperture, a transmission focal point, a transmission frequency, a reception filter band, a reception center frequency, etc.) may be changed.

Figure 23:
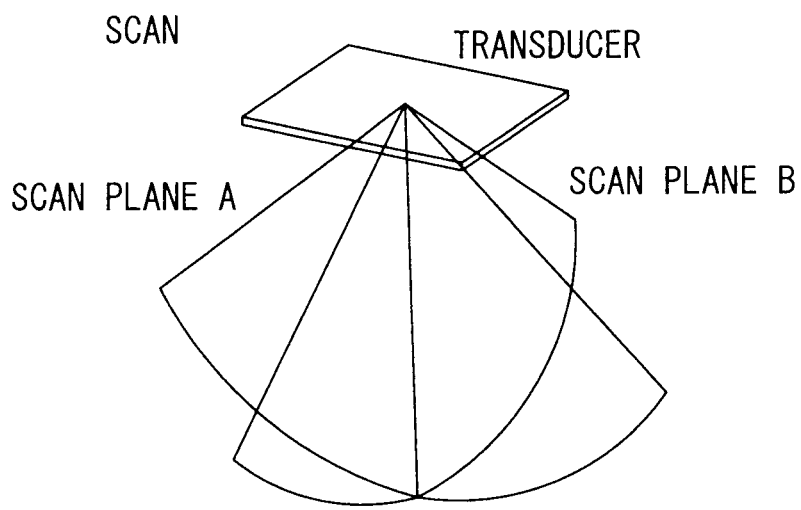
FIG. 23 is an explanatory diagram for describing an ultrasonic wave multi-planar scanning method.

It should be noted that according to the first and second embodiments of the present invention, across the three dimensional region, the plurality of pieces of three dimensional color Doppler mode image data are collected, and the Doppler sample marker tracking control process is performed with use of the volume data after the conversion but the embodiments are not limited to the above-mentioned case. As shown in FIG. 23, for example, the Doppler sample marker tracking control process may be performed with use of a multi-planar scanning for discretely transmitting and receiving an ultrasonic beam.

In addition, according to the first and second embodiments of the present invention, the position of the center of gravity for the blood flow region formed by the blood flow surface is calculated but the embodiments are not limited to the above-mentioned case. It suffices as long as any position in the extracted blood flow region can be calculated. For example, other than the center of gravity, a position mathematically called "center of OO" or the like may be calculated.

Furthermore, according to the first and second embodiments of the present invention, the Doppler sample marker tracking control process is executed with use of the volume data of the blood flow speed but the embodiments are not limited to the above-mentioned case. For example, among the volume data related to the blood flow information, the Doppler sample marker tracking control process may be executed with use of the volume data about the power (signal intensity).

It should be noted that the first and second embodiments of the present invention are applied to the case where the operator performs the diagnosis on the coronary artery of the heart but the embodiments are not limited to the above-mentioned case. The embodiments can be applied to a case where a diagnosis is performed on the blood vessel in any part of the subject body.

It should be noted that the series of the processes described according to the first and second embodiments of the present invention can be executed not only by a software but also by a hardware.

Moreover, the steps in the flowchart in the first and second embodiments of the invention are performed in a time-series manner in the described order, for example, but may be performed in parallel or separately, without limiting to the processing to be performed in a time-series manner.

What is claimed is:

1. An ultrasonic diagnostic apparatus, comprising:
a 3D volume data generation unit configured to oscillate a plurality of ultrasonic wave transducer elements to transmit ultrasonic waves and to receive reflection waves which are reflected from a subject body, and to generate 3D volume data of blood flow speed inside the subject body on the basis of reception signals obtained by converting the reflection waves by the ultrasonic wave transducer elements;
a fluid region extraction unit configured to extract a 3D fluid region by continuously extracting a blood flow surface from the 3D volume data of the blood flow speed, the blood flow surface being a surface where the blood flow speed in the 3D volume data is lower than a predetermined reference value;
a position calculation unit configured to calculate a 3D center position of the 3D fluid region;
a sample marker position setting unit configured to set a 3D position of a sample marker to the 3D center position calculated by the position calculation unit;
a sample marker movement control unit configured to control a movement of the 3D position of the sample marker on the basis of sample marker position setting data set by the sample marker position setting unit; and
a transmission and reception control unit configured to perform a control such that ultrasonic waves are transmitted and received at the 3D position of the sample marker whose movement is controlled by the sample marker movement control unit.

2. The ultrasonic diagnostic apparatus according to claim 1, further comprising:
a spectrum image data generation unit configured to detect a Doppler signal at an observation position of the fluid inside the subject body corresponding to the set 3D position of the sample marker from the reception signals of the transmission and reception of the ultrasonic waves controlled by the transmission and reception control unit on the basis of the sample marker position setting data and generate spectrum image data by performing a predetermined operation on the detected Doppler signal; and
a display unit configured to display a spectrum image based on the spectrum image data.

3. The ultrasonic diagnostic apparatus according to claim 2, further comprising:
a correction factor calculation unit configured to calculate an angle correction factor with use of an angle defined by a longitudinal direction in the 3D fluid region and a beam direction of the ultrasonic waves; and
a scale correction unit configured to correct a scale of the spectrum image data by multiplying the spectrum image data by the angle correction factor,
wherein the display unit displays a spectrum image based on the spectrum image data whose scale is corrected by the scale correction unit.

4. The ultrasonic diagnostic apparatus according to claim 1, further comprising a display unit configured to superpose the sample marker on an image based on image data related to the fluid inside the subject body which is generated with use of the 3D volume data, and displaying the image.

5. The ultrasonic diagnostic apparatus according to claim 1, wherein the 3D center position calculated by the position calculation unit is a center of gravity in the fluid region.

6. The ultrasonic diagnostic apparatus according to claim 1, further comprising:
a binarization unit configured to binarize the 3D volume data; and
a surface extraction unit configured to extract the 3D fluid region on the basis of the binary data of the 3D volume data which is obtained by the binarization unit,
wherein the fluid region extraction unit calculates the 3D fluid region extracted by the surface extraction unit.

7. The ultrasonic diagnostic apparatus according to claim 6, further comprising a weighting unit configured to perform a weighting used for calculating the 3D center position by the position calculation unit, on the basis of the binary data of the 3D volume data that is obtained by the binarization unit,
wherein the position calculation unit calculates the 3D center position of the 3D fluid region with use of a weighting result of the weighting unit.

8. The ultrasonic diagnostic apparatus according to claim 1, wherein the fluid region extraction unit calculates the 3D fluid region on the basis of one of speed information and information related to a signal intensity among the 3D volume data related to the fluid in the subject body.

9. The ultrasonic diagnostic apparatus according to claim 1, further comprising a fluid region shape determination unit configured to calculate, when a plurality of fluid regions are newly extracted, cross-correlation factors between shapes of the newly extracted fluid regions and a shape of the fluid region which has been already extracted and to determine whether or not any one of the newly extracted fluid region shapes is substantially identical to the shape of the already extracted fluid region on the basis of the calculated cross-correlation factors,
wherein only when it is determined that any one of the newly extracted fluid region shapes is substantially identical to the shape of the already extracted fluid region, a movement control process for the sample marker is performed.

10. The ultrasonic diagnostic apparatus according to claim 1, further comprising:
a data obtaining unit configured to obtain data related to a region of interest where a tracking control process of the sample marker is executed; and
a region of interest setting unit configured to set the region of interest where the tracking control process of the sample marker is executed, on the basis of the data related to the region of interest obtained by the data obtaining unit.

11. The ultrasonic diagnostic apparatus according to claim 1, wherein at least one of the volume data generation unit, the fluid region extraction unit, the position calculation unit, and the sample marker position setting unit is driven at a predetermined timing based on an ECG signal detected from the subject body.

12. The ultrasonic diagnostic apparatus according to claim 1, further comprising:
a statistical computation unit configured to perform a statistical computation on the basis of a plurality of pieces of the sample marker position setting data; and
a sample marker width setting unit configured to set a width of the sample marker on the basis of a result of the statistical computation.

13. The ultrasonic diagnostic apparatus according to claim 12, wherein the transmission and reception control unit controls a transmission and reception condition of the ultrasonic waves on the basis of the result of the statistical computation by the statistical computation unit.

14. An ultrasonic diagnostic method, comprising:
a 3D volume data generation step of oscillating a plurality of ultrasonic wave transducer elements to transmit ultrasonic waves and to receive reflection waves which are reflected from a subject body, and generating 3D volume data of blood flow speed inside the subject body on the basis of reception signals obtained by converting the reflection waves by the ultrasonic wave transducer elements;
a fluid region extraction step of extracting a 3D fluid region by continuously extracting a blood flow surface from the 3D volume data of the blood flow speed, the blood flow surface being a surface where the blood flow speed in the 3D volume data is lower than a predetermined reference value;
a position calculation step of calculating a 3D center position of the 3D fluid region;
a sample marker position setting step of setting a 3D position of a sample marker to the 3D center position calculated in a process of the position calculation step;
a sample marker movement control step of controlling a movement of the 3D position of the sample marker on the basis of sample marker position setting data set in a process of the sample marker position setting step; and
a transmission and reception control step of performing a control such that ultrasonic waves are transmitted and received at the 3D position of the sample marker whose movement is controlled in a process of the sample marker movement control step.

15. A non-transitory computer readable medium storing a control processing program for an ultrasonic diagnostic apparatus, which when executed by a computer, causes the computer to execute:
a 3D volume data generation step of oscillating a plurality of ultrasonic wave transducer elements to transmit ultrasonic waves and to receive reflection waves which are reflected from a subject body, and generating 3D volume data of blood flow speed inside the subject body on the basis of reception signals obtained by converting the reflection waves by the ultrasonic wave transducer elements;
a fluid region extraction step of extracting a 3D fluid region by continuously extracting a blood flow surface from the 3D volume data of the blood flow speed, the blood flow surface being a surface where the blood flow speed in the 3D volume data is lower than a predetermined reference value;
a position calculation step of calculating a 3D center position of the 3D fluid region;
a sample marker position setting step of setting a 3D position of a sample marker to the 3D center position calculated in a process of the position calculation step;
a sample marker movement control step of controlling a movement of the 3D position of the sample marker on the basis of sample marker position setting data set in a process of the sample marker position setting step; and
a transmission and reception control step of performing a control such that ultrasonic waves are transmitted and received at the 3D position of the sample marker whose movement is controlled in a process of the sample marker movement control step.

* * * * *